US010294612B2

(12) United States Patent
Medoff et al.

(10) Patent No.: US 10,294,612 B2
(45) Date of Patent: May 21, 2019

(54) CONTROLLING PROCESS GASES

(71) Applicant: XYLECO, INC., Wakefield, MA (US)

(72) Inventors: Marshall Medoff, Brookline, MA (US); Thomas Craig Masterman, Rockport, MA (US); Robert Paradis, Burlington, MA (US)

(73) Assignee: Xyleco, Inc., Wakefield, MA (US)

( * ) Notice: Subject to any disclaimer, the term of this patent is extended or adjusted under 35 U.S.C. 154(b) by 0 days.

(21) Appl. No.: 15/434,629

(22) Filed: Feb. 16, 2017

(65) Prior Publication Data
US 2017/0165628 A1 Jun. 15, 2017

Related U.S. Application Data

(63) Continuation of application No. 14/299,006, filed on Jun. 9, 2014, now Pat. No. 9,611,516, which is a
(Continued)

(51) Int. Cl.
*C10G 1/00* (2006.01)
*C10L 1/02* (2006.01)
(Continued)

(52) U.S. Cl.
CPC ............. *D21C 9/007* (2013.01); *B01D 15/02* (2013.01); *B01D 53/32* (2013.01); *B01D 61/44* (2013.01);
(Continued)

(58) Field of Classification Search
CPC ............. B01J 19/085; B01J 2219/0886; B01J 2219/0879; B01J 2219/0869; B01D 53/32;
(Continued)

(56) References Cited

U.S. PATENT DOCUMENTS 2,820,165 A    1/1958  Robinson
2,985,589 A    5/1961  Broughton et al.
(Continued)

FOREIGN PATENT DOCUMENTS

CN    102076741    5/2011
CN    102802532    11/2012
(Continued)

OTHER PUBLICATIONS

JP 08166497 A (English-language abstract).*
(Continued)

*Primary Examiner* — Nicholas A Smith
*Assistant Examiner* — Colleen M Raphael
(74) *Attorney, Agent, or Firm* — Leber IP Law; Shelly M. Fujikawa

(57) ABSTRACT

Biomass (e.g., plant biomass, animal biomass, and municipal waste biomass) is processed to produce useful intermediates and products, such as energy, fuels, foods or materials. For example, equipment, systems and methods are described that can be used to treat feedstock materials, such as cellulosic and/or lignocellulosic materials, in a vault in which hazardous gases are removed, destroyed and/or converted. The treatments are efficient and can reduce the recalcitrance of the lignocellulosic material so that it is easier to produce an intermediate or product, e.g., sugars, alcohols, sugar alcohols and energy, from the lignocellulosic material.

8 Claims, 5 Drawing Sheets

Related U.S. Application Data continuation of application No. PCT/US2014/021630, filed on Mar. 7, 2014.

(60) Provisional application No. 61/793,336, filed on Mar. 15, 2013, provisional application No. 61/774,761, filed on Mar. 8, 2013, provisional application No. 61/774,735, filed on Mar. 8, 2013, provisional application No. 61/774,754, filed on Mar. 8, 2013, provisional application No. 61/774,744, filed on Mar. 8, 2013, provisional application No. 61/774,731, filed on Mar. 8, 2013, provisional application No. 61/774,684, filed on Mar. 8, 2013, provisional application No. 61/774,740, filed on Mar. 8, 2013, provisional application No. 61/774,746, filed on Mar. 8, 2013, provisional application No. 61/774,752, filed on Mar. 8, 2013, provisional application No. 61/774,750, filed on Mar. 8, 2013, provisional application No. 61/774,775, filed on Mar. 8, 2013, provisional application No. 61/774,780, filed on Mar. 8, 2013, provisional application No. 61/774,723, filed on Mar. 8, 2013, provisional application No. 61/774,773, filed on Mar. 8, 2013.

(51) Int. Cl.

| | | |
|---|---|---|
| *C10L 9/08* | (2006.01) | |
| *C12M 1/00* | (2006.01) | |
| *C12P 7/04* | (2006.01) | |
| *C12P 7/06* | (2006.01) | |
| *C12P 7/10* | (2006.01) | |
| *C12P 7/52* | (2006.01) | |
| *C12P 7/56* | (2006.01) | |
| *C13K 1/02* | (2006.01) | |
| *D21C 9/00* | (2006.01) | |
| *E04B 1/92* | (2006.01) | |
| *G21F 7/00* | (2006.01) | |
| *B01D 15/02* | (2006.01) | |
| *B01D 53/32* | (2006.01) | |
| *B01D 61/44* | (2006.01) | |
| *B01J 19/08* | (2006.01) | |
| *B65G 27/00* | (2006.01) | |
| *B65G 53/04* | (2006.01) | |
| *B65G 53/40* | (2006.01) | |
| *H01J 37/317* | (2006.01) | |
| *C13K 13/00* | (2006.01) | |
| *C12P 19/02* | (2006.01) | |
| *C12P 19/14* | (2006.01) | |
| *C07C 29/149* | (2006.01) | |
| *C07C 31/12* | (2006.01) | |

(52) U.S. Cl.
CPC .......... *B01D 61/445* (2013.01); *B01J 19/085* (2013.01); *B65G 27/00* (2013.01); *B65G 53/04* (2013.01); *B65G 53/40* (2013.01); *C07C 29/149* (2013.01); *C07C 31/12* (2013.01); *C10G 1/00* (2013.01); *C10L 1/023* (2013.01); *C10L 1/026* (2013.01); *C10L 9/08* (2013.01); *C12M 47/00* (2013.01); *C12M 47/10* (2013.01); *C12P 7/04* (2013.01); *C12P 7/06* (2013.01); *C12P 7/10* (2013.01); *C12P 7/52* (2013.01); *C12P 7/56* (2013.01); *C12P 19/02* (2013.01); *C12P 19/14* (2013.01); *C13K 1/02* (2013.01); *C13K 13/002* (2013.01); *E04B 1/92* (2013.01); *G21F 7/00* (2013.01); *H01J 37/317* (2013.01); *B01J 2219/0869* (2013.01); *B01J 2219/0879* (2013.01); *B01J 2219/0886* (2013.01); *C10L 2200/0469* (2013.01); *C10L 2200/0476* (2013.01); *C10L 2290/36* (2013.01); *C12P 2201/00* (2013.01); *C12P 2203/00* (2013.01); *E04B 2001/925* (2013.01); *H01J 2237/202* (2013.01); *H01J 2237/31* (2013.01); *H01J 2237/3165* (2013.01); *Y02E 50/16* (2013.01); *Y02E 50/17* (2013.01); *Y02E 50/30* (2013.01); *Y02E 50/32* (2013.01); *Y02E 50/343* (2013.01); *Y02E 60/17* (2013.01); *Y02P 20/136* (2015.11); *Y02W 10/33* (2015.05); *Y02W 10/37* (2015.05)

(58) Field of Classification Search
CPC ...... B01D 61/44; B01D 15/02; B01D 61/445; H01J 37/317; H01J 2237/202; H01J 2237/3165; H01J 2237/31; C12P 7/10; C12P 19/02; C12P 19/14; C12P 7/04; C12P 2201/00; C12P 7/52; C12P 7/06; C12P 7/56; C12P 2203/00; C12M 47/10; C12M 47/00; C13K 13/002; C13K 1/02; C10L 1/026; C10L 1/023; C10L 2200/0469; C10L 2290/36; C10L 2200/0476; C10L 9/08; C10G 1/00; D21C 9/007; C07C 31/12; C07C 29/149; B65G 53/40; B65G 53/04; B65G 27/00; G21F 7/00; E04B 1/92; E04B 2001/925; Y02W 10/33; Y02W 10/37; Y02E 50/32; Y02E 60/17; Y02E 50/17; Y02E 50/343; Y02E 50/16; Y02P 20/136

See application file for complete search history.

(56) References Cited

U.S. PATENT DOCUMENTS

| | | | |
|---|---|---|---|
| 4,316,747 A | 2/1982 | Rugg et al. | |
| 4,362,965 A | 12/1982 | Kendall | |
| 4,769,082 A | 9/1988 | Kumakura | |
| 5,142,023 A | 8/1992 | Gruber et al. | |
| 5,154,892 A * | 10/1992 | Luhmann | B01J 19/14 |
| | | | 118/65 |
| 5,247,058 A | 9/1993 | Gruber et al. | |
| 5,247,059 A | 9/1993 | Gruber et al. | |
| 5,247,069 A | 9/1993 | Gruber et al. | |
| 5,258,488 A | 11/1993 | Gruber et al. | |
| 5,338,822 A | 8/1994 | Gruber et al. | |
| 5,357,035 A | 10/1994 | Gruber et al. | |
| 5,378,898 A * | 1/1995 | Schonberg | A62D 3/15 |
| | | | 204/157.3 |
| 5,401,973 A | 3/1995 | McKeown et al. | |
| 5,475,080 A | 12/1995 | Gruber et al. | |
| 5,484,881 A | 1/1996 | Gruber et al. | |
| 5,525,706 A | 6/1996 | Gruber et al. | |
| 5,536,807 A | 7/1996 | Gruber et al. | |
| 5,539,081 A | 7/1996 | Gruber et al. | |
| 5,574,129 A | 11/1996 | Miyoshi et al. | |
| 5,585,191 A | 12/1996 | Gruber et al. | |
| 5,665,474 A | 9/1997 | Gruber et al. | |
| 5,763,564 A | 6/1998 | Gruber et al. | |
| 5,773,562 A | 6/1998 | Gruber et al. | |
| 5,798,436 A | 8/1998 | Gruber et al. | |
| 5,807,973 A | 9/1998 | Gruber et al. | |
| 5,849,401 A | 12/1998 | El-Afandi et al. | |
| 5,852,166 A | 12/1998 | Gruber et al. | |
| 5,877,582 A * | 3/1999 | Nishimura | H01J 33/04 |
| | | | 313/35 |
| 5,898,261 A * | 4/1999 | Barker | H01J 33/04 |
| | | | 313/20 |
| 5,981,694 A | 11/1999 | Gruber et al. | |
| 6,005,067 A | 12/1999 | Gruber et al. | |
| 6,005,068 A | 12/1999 | Gruber et al. | |
| 6,093,791 A | 7/2000 | Gruber et al. | |
| 6,111,060 A | 8/2000 | Gruber et al. | |

(56) References Cited

U.S. PATENT DOCUMENTS

| | | |
|---|---|---|
| 6,114,495 A | 9/2000 | Kolstad et al. |
| 6,121,410 A | 9/2000 | Gruber et al. |
| 6,140,458 A | 10/2000 | Terado et al. |
| 6,143,863 A | 11/2000 | Gruber et al. |
| 6,160,173 A | 12/2000 | Eyal et al. |
| 6,183,814 B1 | 2/2001 | Nangeroni et al. |
| 6,207,792 B1 | 3/2001 | Gruber et al. |
| 6,217,630 B1 | 4/2001 | Chanen et al. |
| 6,229,046 B1 | 5/2001 | Eyal et al. |
| 6,277,951 B1 | 8/2001 | Gruber et al. |
| 6,320,077 B1 | 11/2001 | Eyal et al. |
| 6,323,307 B1 | 11/2001 | Bigg et al. |
| 6,326,458 B1 | 12/2001 | Gruber et al. |
| 6,353,086 B1 | 3/2002 | Kolstad et al. |
| 6,355,772 B1 | 3/2002 | Gruber et al. |
| 6,429,280 B1 | 8/2002 | Hiroaka et al. |
| 6,452,051 B1 | 9/2002 | Eyal |
| 6,506,873 B1 | 1/2003 | Ryan et al. |
| 6,528,617 B1 | 3/2003 | Terado et al. |
| 6,534,679 B2 | 3/2003 | Eyal et al. |
| 6,724,003 B1 | 4/2004 | Doi et al. |
| 6,740,731 B2 | 5/2004 | Bigg et al. |
| 6,846,657 B2 | 1/2005 | Heikkilaet et al. |
| 7,019,170 B2 | 3/2006 | Eyal et al. |
| 7,026,145 B2 | 4/2006 | Mizrahi et al. |
| 7,083,955 B2 | 8/2006 | Otto |
| 7,098,009 B2 | 8/2006 | Shanmugam et al. |
| 7,144,977 B2 | 12/2006 | Eyal et al. |
| 7,186,541 B2 | 3/2007 | Gokam et al. |
| 7,217,545 B2 | 5/2007 | Agblevor et al. |
| 7,273,734 B2 | 9/2007 | Minami et al. |
| 7,309,597 B2 | 12/2007 | Liao et al. |
| 7,393,676 B2 | 7/2008 | Gokam et al. |
| 7,638,316 B2 | 12/2009 | Gokam et al. |
| 7,932,065 B2 | 4/2011 | Medoff |
| 8,030,045 B2 | 10/2011 | Jessen et al. |
| 8,076,120 B2 | 12/2011 | Gokam et al. |
| 8,088,427 B2 | 1/2012 | Engleson et al. |
| 8,173,753 B2 | 5/2012 | Nagano et al. |
| 8,198,066 B2 | 6/2012 | Gokam et al. |
| 8,728,770 B2 | 5/2014 | Ishikawa |
| 9,611,516 B2 * | 4/2017 | Medoff ............... B01J 19/085 |
| 9,659,748 B2 * | 5/2017 | Medoff ............... B01J 19/085 |
| 2002/0135290 A1 | 9/2002 | Avnery |
| 2004/0113094 A1 | 6/2004 | Lyons et al. |
| 2004/0183032 A1 | 9/2004 | Fink et al. |
| 2006/0260928 A1 | 11/2006 | Avnery |
| 2008/0313954 A1 | 12/2008 | Lee |
| 2011/0236945 A1 | 9/2011 | Maclachian et al. |
| 2012/0100577 A1 | 4/2012 | Medoff et al. |
| 2012/0136196 A1 | 5/2012 | Foxall |
| 2012/0316376 A1 | 12/2012 | Medoff |

FOREIGN PATENT DOCUMENTS

| | | |
|---|---|---|
| EP | 1568888 | 8/2005 |
| EP | 2172568 | 4/2010 |
| JP | S63-185444 | 8/1988 |
| JP | H6-51900 | 7/1994 |
| JP | 08-166497 | 6/1996 |
| JP | 08166497 A * | 6/1996 |
| JP | H08-166498 | 6/1996 |
| JP | 09262528 | 10/1997 |
| JP | 11106206 | 4/1999 |
| JP | 2001108800 | 4/2001 |
| JP | 2001-318196 | 11/2001 |
| JP | 2002-045159 | 2/2002 |
| JP | 2002-085032 | 3/2002 |
| JP | 2012527241 A | 11/2012 |
| WO | 199324704 | 12/1993 |
| WO | 199503374 | 2/1995 |
| WO | 2007009463 | 1/2007 |
| WO | 2014059140 | 4/2014 |

OTHER PUBLICATIONS

Machine translation of the description of JP 2001-318196 (Year: 2001).*

Machine translation of the description of JP 2002-045159 (Year: 2002).*

Machine translation of the description of JP 2002-085032 (Year: 2002).*

Office Action dated Feb. 22, 2017, issued by the European Patent Office in corresponding EP Application No. 14760007.6 (6 pages).

Zheng et al. "Overview of biomass pretreatment for cellulosic ethanol production," Int J Agric & Biol Eng, vol. 2 No. 3, pp. 51-68 (2009).

Written Opinion dated Mar. 16, 2017 issued by the Intellectual Property Office of Singapore in corresponding SG Application No. 11201502358X (6 pages).

Haug, G. "Aspects of Rotary Vacuum Filter Design & Performance," Reprint from Fluid/Particle Separation Journal. vol. 13(1) Apr. 2000 (19 pages).

BHS Sonthofen GmbH—BF Indexing Belt Filter "Gentle Filtration of Sedimenting Media." www.bhs-sonthofen.com 2012 (16 pages).

Technical Bulletin by Osprey Corporation, Spring 2004 (2 pages).

Filter Cloth by Kavon Filter Product Co., Feb. 26, 2012 (3 pages).

Rotary Drum Vacuum Filter by Komine-Sanderson, 1996 (8 pages).

BHS Sonthofen GmbH—RPF Rotary Pressure Filter "Precise Separation of Suspensions," www.bhs-sonthofen.com 2012 (12 pages).

Filter Cloth by Suita Group, Feb. 26, 2013, (3 pages), www.filtercloths.cn.

"An Introduction to Steam Boilers and Steam Raising" by N.E.M. Business Solutions. Nov. 15, 2012, (23 pages), www.cip.ukcentre.com/steam.htm.

Stempek, J.R. et al., A Technical Paper, "Innovative Solutions for a Challenging Biomass Fuel and Boiler Upgrade Project," TAPPI Engineering Pulping, Environmental Conference, Aug. 28-31, 2005 (11 pages).

Cellulose Ethanol (Cellulosic Ethanol), www.zfacts.com (Feb. 27, 2013, 4 pages).

Technical Study Report on "Biomass Fired—Fluidized Bed Combustion Boiler Technology for Cogeneration" by UNEP, www.uneptie.fr/energy (Sep. 2007, 68 pages).

"Biomass Conversion Technologies," Chapter 5, EPA, Combined Heat and Power Partnership : Biomass CHP Catalog, (32 pages), www.epa.gov (Accessed Jun. 12, 2014).

"Holo-Flite Thermal Processor," Metso Minerals Industries, Inc. (2012, 8 pages).

Kamp, P. "Inbicon Biomass Refinery Cellulosic Ethanol Technology Platforms, Growth and Sustainability through Biomass Refining, CHP—Technology Review" Inbicon Leifmark, North America Business Development (2010, 40 pages).

"Thermal Degradation of Wood Components: A Review of the Literature," U.S.D.A. Forest Service Research Paper FPL 130 (May 1970, 29 pages).

Belderock, H.J.M. Master Thesis entitled "Experimental Investigation and Modeling of the Pyrolysis of Biomass," Eindhoven University of Technology, The Netherlands (Dec. 2007, 125 pages).

Cleland, M.R., "Industrial Applications of Electron Accelerators," Ion Beam Applications, Edgewood, NY 11717, USA http://cds.cem.ch/record/1005393/files/p383.pdf?version=1 (Accessed Jun. 12, 2014, 34 pages).

Krumeich, F., "Properties of Electrons, Their interactions with Matter and Applications in Electron Microscopy," Laboratory of Inorganic Chemistry, ETH Zurich, HCI-1111, CH-8093 Zurich http://www.microscopy.ethz.ch/downloads/interactions.pdf (Accessed Jun. 12, 2014, 23 pages).

Author Unknown, "The Case for Geothermal," www.gladwell.com (Aug. 7, 2008, 10 pages).

"Recommendations for Geothermal Heating and Cooling Systems." State of Ohio, Ohio Water Resources Council. State Coordinating Committee on Ground Water (Feb. 2012, 32 pages).

Swanson, K., "Broadbeam—Getting Started with EB," PCT Engineered Systems (2012, 9 pages).

"Guidelines for Ozone Mitigation at the APS," Advanced Photon Source, (May 1994, 20 pages).

(56) References Cited

OTHER PUBLICATIONS

Gundel, L.A. et al, "A Pilot Study of Energy Efficient Air Cleaning for Ozone," Indoor Environmental Department, Environmental Energy Technologies Division, Lawrence Berkeley National Laboratory, Berkeley, CA (Nov. 28, 2002, 14 pages).
"Product Bulletin: Ozone Destruct Unit," Corporate Consulting Service Instruments, Inc., Manufactured in Akron, Ohio 44301 USA http://www.ccsi-inc.com/pb-ozone-destruct.pdf (Assessed Jun. 12, 2014, 2 pages).
Shepherd, A. "Activated Carbon Adsorption for Treatment of VOC Emissions," Presented at the 13th Annual EnviroExpo, Boston, MA (May 2001, 4 pages).
Fare, T.L. et al. "Effects of Atmospheric Ozone on Microarray Data Quality," Analytical Chemistry (2003, 4 pages).
Swanson, W.P. et al. "Toxic Gas Production at Electron Linear Accelerators," Standard Linear Accelerated Center, Stanford University, Stanford, California 94305 (Feb. 1980, 11 pages).
"The advantage of physically separating airflow for each conveyor," Air Flow Two Technology by Extru-Tech, Inc. www.extru-techinc.com (Accessed Jun. 12, 2014, 4 pages).
"DustBeater, DBS and DB12 Models with MLOS Control—User Guide," The Conair Group, Inc. Pittsburgh, PA 15202 www.conairnet.com (2002, 68 pages).
"TLM Model Tube Loaders, Hopper Loading and Direct Feed Configurations with MLC2 Control—User Guide,"for The Conair Group, Inc. Pittsburg, PA 15202 www.conairnet.com (2002, 45 pages).
"TLA Model Tube Loaders. Hopper Loading. Feeding Bin and Direct Feed Configurations—User Guide," for The Conair Group, Inc. Pittsburgh, PA 15202 www.conairnet.com (2003, 38 pages).
"Biomass Technology Review," Prepared for Biomass Power Association by McHale & Associates, Inc., Oct. 21, 2010 (52 pages).
"Access Loader with Easy Loader Control (ELC), Models AL2 and AL5—User Guide," for the Conair Group Inc., Pittsburg, PA 15202 www.containret.com (2008, 109 pages).
"CAML-EVG Compressed Air Material Evacuator—User Guide," for The Conair Group, Inc. Pittsburg, PA 15202 www.conairnet.com (2001, 48 pages).
Abdel-Rahman, M.A. et al., "Lactic Acid Production from Lignocellulose-Derived Sugars Using Lactic Acid Bacteria Overview and Limits," J. Biotechnical., vol. 156, 296-301 (2011).
Moniz-Xavier, A.M.M. Master Thesis entitled "Study of Lactic Acid Polycondensation and Lactide Production." Developed for the Dissertation Project realized in Eidgenossische Technische Hochschule Zurich, for Universidade do Porto (Jul. 2010, 71 pages).
Mukhopadhyay, A., A Thesis entitled, "Bioconversion of Paper Mill Lignocellulosic Materials to Lacid Acid Using Cellulase Enzyme Complex and Microbial Cultures," prepared for Department of Grain Science and Industry College of Agriculture, Kansas State University, Manhattan, Kansas (2009, 60 pages).
Ahmed, J. and Varsheney, S.K., "Polyactides-Chemistry, Properties and Green Packaging Technology: A Review," Intl. J. Food Properties, vol. 14(1), 37-58 (2011).
Xiao, Y., A Thesis entitled, "Functional Polymers by Enzymatic Catalysis," Supported by Marie Curie Action RTN program Biocatalytic Approach in Material Design, Contract No. MRTN-CT-2004-505147 (2009, 148 pages).
Abdel-Rahman, M. et al., Efficient Homofementative L-(+)-Lactic Acid Production from Xylose by a Novel Lactic Acid Bacterium. *Enterococcus mundtii* QU 25, Appl. Environ. Microbiol., vol. 77(5) 1892-1895 (Mar. 2011).
Miller, D.J. and Dodge, B.R., "Biochemical From Corn: Update 2008," for Ontario BioAuto Council, Ontario Agri-Food Technologies, Ontario Ministry of Agriculture, Good and Rural Affairs (48 pages).
Wang, L. et al., "Efficient production of L-lactic acid from corncob molasses, a waste by-product to xylitol production, by a newly isolated xylose utilizing *Bacillus* sp strain," Bioresour, Technol (2010, 8 pages).

Hassan, E. et al., "Dynamic Mechanical Properties and Thermal Stability of Poly(lactid acid) and Poly(butylene succinate) Blends Composites," J. Fiber Bioengineer, Inform., vol. 6(1): 85-94 (2013).
Osmundsen, C.M., "Catalysis & Biomass: Strategies for Biomass Conversion to Fuels and Chemicals," for Haldor Topsoe/DTU (Mar. 2011, 39 pages).
Chen, C.D. and Ju, L-K., "Coupled Lactic Acid Fermentation and Adsorption," Appl. Microbial Biotechnol, vol. 59, 170-174 (2002).
Dutkiewicz, S. et al., "Synthesis of Poly(L(+) Lactic Acid) by Polycondensation Method in Solution," Fibres & Textiles in Eastern Europe, vol. 11(4)(43): 66-70 (Dec. 2003).
Edreder, E.A. et al., "Optimization of Batch Reactive Distillation Process. Production fo Lactic Acid." 20th European Symposium on Computer Aided Process Engineering—ESCAPE20, Ed. S. Pierucci and H. Buzzi Ferraris (2010, 6 pages).
Malinowski, R. et al. "Effects of Electron Radiation on Properties of PLA," Archives of Materials Science and Engineering,vol. 49(1) 25-32 (May 2011).
Fakhravar, S. et al., "Fermentative Lactic Acid from Deproteinized Whey Using Lactobacillus bulgaricus in Batch Culture," World Applied Sciences Journal, vol. 17(9): 1083-1086 (2012).
Garlotta, D., "A Literature Review of Poly(Lactic Acid)," J. Polymers and the Environ., vol. 9(2): 63-64 (2001).
Habova, V. et al., "Modern Method of Lactic Acid Recovery from Fermentation Broth," Czech J. Food Sci., vol. 22(3) 87-94 (2004).
Halasz, K. and Csoka, L., "Plasticized Biodegradable Poly(lactic acid) Based Composites Containing Cellulose in Micro-and Nanosize," J. Engineer, vol. 2013, Article ID 329379 (2012, 9 pages).
Henton, D.E., "Polylactic Acid Technology," Ch. 16, in Natural Fibers, Biopolymers, and Biocomposites http://www.iimluntllc.com/pdfs/polylactic_acid_technology.pdf (Accessed Jun. 12, 2014, pp. 527-577).
Walton, S. et al., "Production of lactic acid from hemicellulose extracts by Bacillus coagulans MXL-9," J. Ind. Microbiol. Biotechnal., vol. 37: 823-830 (2010).
INGEO Resin Product Guide, for NatureWorks LLC., www.natureworksllc.com (2011, 4 pages).
Jonglertjunya,W. et al., "Utilization of Sugarcane Bagasses for Lactic Acid Production by Acid Hydrolysis and Fermentation Using *Lactobacillus* sp.," World Academy of Science, Engineering and Technology, vol. 66: 173-178 (2012).
Liu, L. et al., "Phosphoketolase Pathway for Xylose Catabolism in Clostridium acetoculicum Revealed by C. Metabolic Flux Analysis," J. Bacteriol., vol. 194(19): 5413-5422 (Oct. 2012).
Lunt, J. and Shafer, A.L., "Polylactic Acid Polymers from Corn—Applications in the Textiles Industry," for Cargill Dow Polymers LLC., Minnetonka, MN 55345 http://jimluntllc.com/pdsf/PolylacticAcidPolymersFrom Corn.pdf (Accessed Jun. 12, 2014, 8 pages).
Maas, R.H.W. et al., "Lactic Acid Production From Xylose by the Fungus Rhizopus Oryzae," Appl. Microbiol. Biotechnol., vol. 72: 861-868 (2006).
Middleton, J.C. and Tiplon A.J., "Synthetic Biodegradable Polymers as Orthopedic Devices," Biomaterials, vol. 21:2335-2346 (2000).
Narayanan, M. et al., "L(+)lactic acid fermentation and its product polymerization," Elect. J. of Biotechnol., vol. 7(2) (2004, 13 pages).
Neureiter, M. et al., "Lignocellulose Feedstocks for the Production of Lactic Acid," Chem. Biochem. Eng Q., vol. 18(1) 55-63 (2004).
Oh, H. et al., "Lactic Acid Production Through Cell-Recycle Repeated-Batch Bioreactor," Appl. Biochem. Biotechnol., vol. 105-108: 603-613 (2003).
Sriwongsa, K. et al., "Radiation-induced Crosslinking of Polylactic Acid: Effects of Air and Vacuum," for TIChE International Conference at Hatyai, Songkhla Thailand (Nov. 10-11, 2011, 5 pages).
Razak, S., et al., "Biodegradable Polymers and their Bone Applications: A Review," Intl. J. Basic & Applied Sciences. vol. 12(1): 31-49 (2012).
Moon, S.L., et al., "Melt Polycondensation of L-Lactic Acid with Sn(II) Catalysts Activated by Various Proton Acids: A Direct Manufacturing Route to High Molecular Weight Poly(L-lactic acid)," J. Polymer Science: Part A: Polymer Chemistry, vol. 38: 1673-1679 (2000).

(56) References Cited

OTHER PUBLICATIONS

Technology Focus Report: Blends of PLA with Other Thermoplastics, for NatureWorks LLC. www.natureworksllc.com (2007, 6 pages).
Ahmed, J. et al., "Thermal Properties of Polylactides," Thermal Analysis and Calorimetry vol. 95(3): 957-964 (2009).
Anuar, H. and Zuraida, A., "Thermal Properties of Injection Moulded Polylactic Acid—Kenaf Fibre Biocomposite" Malaysian Polymer J., vol. 6(1): 51-57 (2011).
Werpy, T. et al., "Top Value-Added Chemicals from Biomass, vol. 1—Results of Screening for Potential Candidates from Sugars and Synthesis Gas," by Pacific Northwest National Laboratory, for U.S. Department of Energy (Aug. 2004, 76 pages).
Holladay, J.E. et al., "Top Value-Added Chemicals from Biomass, vol. II—Results of Screening for Potential Candidates from Biorefinery Lignin," by Pacific Northwest National Laboratory, for U.S. Department of Energy under Contract DE-AC05-76RL01830 (Oct. 2007, 87 pages).
Wang, N. et al., "Synthesis, characterization, biodegradation, and drug delivery application of biodegradable lactic / glycolic acid acid polymers: I. Synthesis and characterization," J. Biomater. Sci. Poly Edn., vol. 11(3) 301-318 (2000).
Wee, Y-J et al., "Biotechnological Production of Lactic Acid and its Recent Applications," Food Techol., Biotechnol., vol. 44(2): 163-172 (2006).
Xiao, L. et al., "Poly(Lactic Acid)-Based Biomaterials: Synthesis, Modification and Applications," Biomedical Science, Engineering and Technology http://www.intechopen.com/books/biomedical-science-engineering-and-technology/polylactic-acid-based-biomaterials-synthesis-modification-and-applications (Accessed Jun. 12, 2014 38 pages).
Zhang, W-x and Wang, Y-z, "Synthesis and Properties of High Molecular Weight Poly(Lactic Acid) and its Resultant Fibers," Chinese J. Polymer Sci., vol. 26(4): 425-432 (2008).
Search Report—Corresponding European Application No. 14760007, dated Jun. 21, 2016, 2 pages.
Search Report—Corresponding Singapore Application No. 11201502358X, dated Jun. 15, 2016, 5 pages.
Taherzadeh, M. et al., "Pretreatment of Lignocellulosic Wastes to Improve Ethanol and Biogas Production: A Review", International Journal of Molecular Sciences, Sep. 1, 2008, vol. 9, No. 9, pp. 1621-1651.
Search Report—Corresponding Chinese Application No. 2014800102253, dated Aug. 24, 2016, 2 pages.
Office Action—Corresponding Japanese Application No. 2015-561698, dated Sep. 19, 2017, 5 pages.
Office Action—Corresponding Egyptian Application No. 2015081342, dated Dec. 19, 2017, 6 pages.

\* cited by examiner

CONTROLLING PROCESS GASES

CROSS REFERENCE TO RELATED APPLICATIONS

This application is a continuation of U.S. patent application Ser. No. 14/299,006, filed Jun. 9, 2014, which is a continuation application of PCT/US14/21630 filed Mar. 7, 2014, which claims priority to the following provisional applications: U.S. Ser. No. 61/774,684, filed Mar. 8, 2013; U.S. Ser. No. 61/774,773, filed Mar. 8, 2013; U.S. Ser. No. 61/774,731, filed Mar. 8, 2013; U.S. Ser. No. 61/774,735, filed Mar. 8, 2013; U.S. Ser. No. 61/774,740, filed Mar. 8, 2013; U.S. Ser. No. 61/774,744, filed Mar. 8, 2013; U.S. Ser. No. 61/774,746, filed Mar. 8, 2013; U.S. Ser. No. 61/774,750, filed Mar. 8, 2013; U.S. Ser. No. 61/774,752, filed Mar. 8, 2013; U.S. Ser. No. 61/774,754, filed Mar. 8, 2013; U.S. Ser. No. 61/774,775, filed Mar. 8, 2013; U.S. Ser. No. 61/774,780, filed Mar. 8, 2013; U.S. Ser. No. 61/774,761, filed Mar. 8, 2013; U.S. Ser. No. 61/774,723, filed Mar. 8, 2013; and U.S. Ser. No. 61/793,336, filed Mar. 15, 2013. The full disclosure of each of these applications is incorporated by reference herein.

BACKGROUND OF THE INVENTION

Many potential lignocellulosic feedstocks are available today, including agricultural residues, woody biomass, municipal waste, oilseeds/cakes and seaweed, to name a few. At present, these materials are often under-utilized, being used, for example, as animal feed, biocompost materials, burned in a co-generation facility or even landfilled.

Lignocellulosic biomass includes crystalline cellulose fibrils embedded in a hemicellulose matrix, surrounded by lignin. This produces a compact matrix that is difficult to access by enzymes and other chemical, biochemical and/or biological processes. Cellulosic biomass materials (e.g., biomass material from which the lignin has been removed) is more accessible to enzymes and other conversion processes, but even so, naturally-occurring cellulosic materials often have low yields (relative to theoretical yields) when contacted with hydrolyzing enzymes. Lignocellulosic biomass is even more recalcitrant to enzyme attack. Furthermore, each type of lignocellulosic biomass has its own specific composition of cellulose, hemicellulose and lignin.

SUMMARY

Generally, the inventions relate to methods, equipment and systems for treating materials, such as biomass. The inventions also relate to methods, systems and processing equipment used for producing products from a biomass material. Generally, the methods include treating a recalcitrant biomass, (e.g., with electron beams or other ionizing radiation) to reduce the recalcitrance of the biomass, optionally while conveying the biomass using one or more conveyor(s) and optionally in an enclosure, such as a vault. Included in the methods, hazardous and/or noxious gases which are produced can be filtered or destroyed. In some implementations, the methods further include biochemically and/or chemically processing the reduced recalcitrance material to, for example, ethanol, xylitol and other useful and valuable products.

Radiation in a confined space containing gases and/or organic material (e.g., air, biomass and/or hydrocarbons), can create reactive gases, e.g., ozone, oxides of nitrogen and/or Volatile Organic Compounds (VOCs), such as methane, ethane, ethylene, formic acid, acetic acid, methanol, formaldehyde, acetaldehyde and acetylene, and/or other airborne agents e.g., Hazardous Air Pollutants (HAPs), such as soot. In addition, accidental release of processing gases from equipment, such as $SF_6$, can be a hazard. The gases can degrade processing equipment and cause equipment wear and failure, incurring costs due to downtime and necessary repairs. The gases also should be removed (e.g., removed, sequestered, filtered, concentrated) and/or destroyed before operators can access the interior of the confined spaces. Finally, the gases should be isolated (e.g., removed, sequestered, filtered) and/or destroyed prior to being released into the environment. Mitigation of these issues can be accomplished by controlling the atmosphere inside the confined space or near the processes, for example, by flushing and/or purging a processing vault with an inert gas (e.g., nitrogen or argon), and ensuring that any process gases are removed from the vault. In addition, any hazardous gases can be filtered and/or destroyed by a filtering system.

In some instances, the invention relates to methods for processing materials (e.g., biomass including lignocellulosic, cellulosic or starchy material). The method includes impinging a substantially inert gas on a foil window of an electron beam horn while passing electrons through the window and inert gas while processing the material. The foil can have a surface communicating with a high vacuum side of an accelerator tube. The foil, along with a secondary foil can define a space about which the substantially inert gas traverses. Optionally, the pressure inside the space is greater than atmospheric pressure (e.g., between about 50 and 200 psi). The inert gas can include nitrogen (e.g., at least 80% nitrogen, at least 90% nitrogen, at least 95% nitrogen, at least 99% nitrogen). Optionally the method includes recycling the inert gas, for example, the inert gas can be impinged on the foil window more than one time before it is discarded. The inert gas can be processed or treated, for example, prior to or before being utilized, or before using the gas again in the method that includes recycling the gas. Optionally, the inert case is treated after impinging electrons on the foil window. Optionally, treating the gas includes filtering the gas. For example, treating the inert gas can include removing from the inert gas contaminants or undesired components that include oxygen, ozone, oils, particulates, water and mixtures thereof. Treating can also include removing volatile organic compounds.

In some cases the invention relates to systems for processing materials, e.g., biomass, where the system includes a flow path for providing a substantially inert gas through a space, wherein the space is defined by, a first foil in communication with the vacuum side of a scanning horn of an electron beam accelerator and a secondary foil disposed facing the first foil window. Optionally, the secondary foil can be mounted on an enclosure. The flow path can optionally include a first conduit and inlet for flowing the inert gas into the space and a second conduit and outlet for flowing the inert gas out of the space. The first and second conduit are in fluid communication through the space. The first conduit and/or inlet and second conduit and/or outlet can be sized so that the pressure inside the space is above atmospheric pressure (e.g., between about 50 and 200 psi).

In another aspect of the invention, the methods include reducing the recalcitrance of biomass (e.g., biomass) while producing or generating a hazardous gas. For example hazardous gases can include gases selected from the group consisting of ozone, volatile organic compounds, hazardous air pollutants, particulates, soot, nitrogen oxides and mixtures of these. The methods include flowing the hazardous gas through a filtering system. The hazardous gas can include a hazardous component and a non-hazardous component and the filtering system is configured to removed and/or destroy by the hazardous component. Optionally, the filter system can include a carbon filter disposed in the flow of the hazardous gas. Optionally, the method includes conveying the biomass while reducing its recalcitrance.

Optionally, reducing the recalcitrance of the biomass material occurs in a vault. For example, the concentration of hazardous gas can be reduced by flowing gas that is in the vault through the filter system to the exterior of the vault and flowing gas from the exterior of the vault to the interior of the vault. For example, a make-up gas is flowed from the exterior of the vault to the interior of the vault while the hazardous gas is flowed from the interior of the vault to the exterior of the vault and through the filtering system. The filtering system can be disposed outside of the vault or inside the vault. Optionally, gas flowing from the exterior of the vault (e.g., a make-up gas) comprises an inert gas. Also optionally, the method can include maintaining a negative pressure in the vault by flowing the gas that is in the vault (e.g., through the filter system) to the exterior of the vault at a faster flow rate than flowing the gas from the exterior of the vault to the interior of the vault (e.g. the make-up gas). For example, the flow rate to the exterior of the vault is at least 2 times faster than the flow rate to the interior of the vault (e.g., at least 3 times faster, at least 4 times faster, at least 5 times faster). In some instances, the flow rate to the exterior of the vault is between about 1000 and 10000 CFM and the flow rate to the interior of the vault is between about 10 and 5000 CFM. Optionally, the method can include conveying the biomass from the interior of the vault to the exterior of the vault, extracting hazardous gases from the biomass, and flowing the hazardous gases through the filter system. For example, the hazardous gases can be extracted from the biomass in the vault or the hazardous gases can be extracted from the biomass once it has been conveyed out of the vault.

Optionally, the recalcitrance of the biomass material can be reduced by exposing the biomass material to ionizing radiation. For example, the ionizing radiation can be produced by an electron accelerator comprising a scanning horn equipped with a metal foil electron extraction window, and the method can further include directing a gas (e.g., a cooling gas) against the extraction side of the foil electron extraction window.

In some aspects, the invention includes a system for processing a material in a vault. The vault can contain an electron irradiation device configured to irradiate a biomass material, e.g., while it is conveyed on a conveyor. The system can also include a process gas treating system, e.g., a system for treating gases produced during the processing of the biomass. Optionally the process gas treating system includes a gas path from the exterior of the vault to the interior of the vault, the gas path continuing through the vault, and then the gas path continuing from the interior of the vault to the exterior of the vault. A filter can be placed in the gas path. For example, the filter can be placed inside the vault in the gas path or outside of the vault in the gas path. The filter can be placed outside the vault and configured to process gasses that flow through the vault (e.g., process gases). The gas path through the vault can include a gas path through a window cooling system. For example, the window cooling system can include a manifold configured to accept a gas from a conduit and the manifold can be also configured for impinging the gas against a first window mounted on the vacuum side of a scan horn of the irradiation device. The window cooling system can also include a second window facing the first window, wherein the first and second window define a space and the space includes an outlet configured to allow the gas to exit the space. For example, the gas path can include a path through the space. Optionally, the gas path through the vault includes a path through an intake manifold.

The equipment, systems and methods described herein are effective in mitigating process gases produced during biomass processing.

Implementations of the invention can optionally include one or more of the following summarized features. In some implementations, the selected features can be applied or utilized in any order while in other implementations a specific selected sequence is applied or utilized. Individual features can be applied or utilized more than once in any sequence and even continuously. In addition, an entire sequence, or a portion of a sequence, of applied or utilized features can be applied or utilized once repeatedly or continuously in any order. In some optional implementations, the features can be applied or utilized with different, or where applicable the same, set or varied, quantitative or qualitative parameters as determined by a person skilled in the art. For example, parameters of the features such as size, individual dimensions (e.g., length, width, height), location of, degree (e.g., to what extent such as the degree of recalcitrance), duration, frequency of use, density, concentration, intensity and speed can be varied or set, where applicable as determined by a person of skill in the art.

Features, for example, include: a method of processing a material; impinging a substantially inert gas on a foil window of an electron beam horn and passing electrons through the window and inert gas while processing a material; a foil that has a surface communicating with a high vacuum side of an accelerator tube; a foil and a secondary foil that defines a space about which a substantially inert gas traverses; a pressure inside a space (e.g., defined by a foil and a secondary foil) that is greater than atmospheric pressure; an inert gas that comprises nitrogen; recycling an inert gas; impinging a substantially inert gas on a foil window more than one time before discarding it; treating an inert gas; treating an inert gas by a method that includes filtering the gas; removing oxygen from an inert gas; removing ozone from an inert gas; removing oils from an inert gas; removing particulates from an inert gas; removing water from an inert gas; processing a biomass material; processing a lignocellulosic material; processing a cellulosic material; utilizing vaults constructed with low porosity bricks.

Features, for example, can also include: a system for processing biomass; a flow path for providing a substantially inert gas through a space, wherein the space is defined by a first foil in communication with the vacuum side of a scanning horn of an electron beam accelerator and a secondary foil disposed facing the first foil; a secondary foil that is mounted on an enclosure; a flow path that includes a first conduit and an inlet for flowing an inert gas into a space and a second conduit and an outlet for flowing the inert gas out of the space, wherein the first conduit and second conduit are in fluid communication through the space; a first conduit and/or inlet and a second conduit and/or outlet that are sized so that the pressure inside the space is greater than atmospheric pressure.

Features, for example, can also include: a method for processing a biomass material; producing a hazardous gas while reducing the recalcitrance of a biomass material, and flowing the hazardous gas through a filtering system; reducing the recalcitrance of a biomass material in a vault; a filtering system disposed outside of a vault for filtering process gases generated inside the vault; a make-up gas that is flowed from the exterior of the vault to the interior of the vault while a hazardous gas is flowed from the interior of the vault to the exterior of the vault and through a filtering system; a make-up gas for a vault that comprises an inert gas; maintaining a negative pressure in a vault by flowing a gas that is in the vault through a filtering system to the exterior of the vault at a faster flow rate than flowing a make-up gas from the exterior of the vault to the interior of the vault; maintaining a negative pressure in a vault by flowing a gas that is in the vault through a filtering system to the exterior of the vault at a flow rate that is at least two times faster than flowing a make-up gas from the exterior of the vault to the interior of the vault; maintaining a negative pressure in a vault by flowing a gas that is in the vault through a filtering system to the exterior of the vault at a flow rate that is at least three times faster than flowing a make-up gas from the exterior of the vault to the interior of the vault; maintaining a negative pressure in a vault by flowing a gas that is in the vault through a filtering system to the exterior of the vault at a flow rate that is at least four times faster than flowing a make-up gas from the exterior of the vault to the interior of the vault; maintaining a negative pressure in a vault by flowing a gas that is in the vault through a filtering system to the exterior of the vault at a flow rate that is at least five times faster than flowing a make-up gas from the exterior of the vault to the interior of the vault; maintaining a negative pressure in a vault by flowing a gas that is in the vault to the exterior of the vault at a rate of between 1000 and 10,000 CFM and flowing a make-up gas from the exterior of the vault to the interior of the vault at a flow rate of between about 10 and 5000 CFM; utilizing a vault constructed of low porosity materials; utilizing a vault constructed of low porosity concrete; utilizing a vault with walls constructed of low porosity bricks; conveying a biomass from the interior of a vault to the exterior of the vault, extracting hazardous gases from the biomass, and flowing the hazardous gases through a filter system; reducing the recalcitrance of the biomass material by exposing the biomass material to ionizing radiation; producing ionizing radiation by an electron accelerator comprising a scanning horn equipped with a metal foil electron extraction window, and directing a cooling gas against the extraction side of the foil electron extraction window; a gas filtering system that includes a carbon filter disposed in the flow of a hazardous gas; a hazardous gas that includes ozone; a hazardous gas that includes volatile organic compounds; conveying a biomass material while reducing the recalcitrance of the biomass material; a hazardous gas that includes a hazardous component and a non-hazardous component and a filtering system that is configured to remove the hazardous component; a hazardous gas that includes a hazardous component and a non-hazardous component and a filtering system that is configured to destroy the hazardous component.

Features, for example, can also include: a system for processing a material in a vault; a vault containing an electron irradiation device configured to irradiate a biomass material, and a process gas treating system comprising a gas path that includes a path from the exterior of the vault to the interior of the vault, through the vault, and to the exterior of the vault; a gas filter in a gas path; a gas path through a vault includes a gas path through a window cooling system and the window cooling system comprises a manifold configured to accept a gas from a conduit and impinging the gas against a first window mounted on the vacuum side of a scan horn of an irradiation device; a window cooling system that includes a first window mounted on the vacuum side of a scan horn of an irradiation device and a second window facing the first window, wherein the first and second window define a space and the space includes an outlet configured to allow the gas to exit the space; a gas path through a vault that includes a path through an intake manifold; a filter that is positioned outside of a vault and configured to filter a gas that has flowed through the vault.

Other features and advantages of the invention will be apparent from the following detailed description, and from the claims.

DETAILED DESCRIPTION

Figure 1:
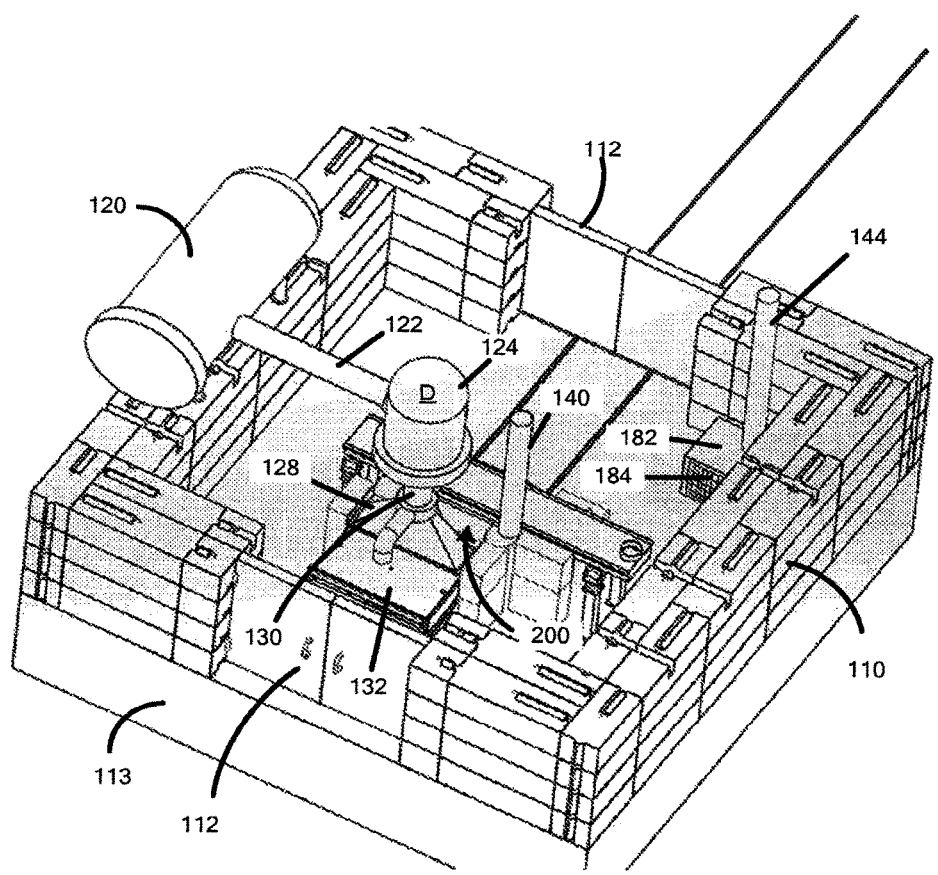
FIG. 1 shows an embodiment of the invention, including a perspective view of a vault with its roof and ceiling not shown and some components of a process gas mitigation system.

Using the equipment, methods and systems described herein, cellulosic and lignocellulosic feedstock materials, for example, that can be sourced from biomass or processed biomass (e.g., plant biomass, animal biomass, paper, and municipal waste biomass) and that are generally readily available, can be turned into useful products (e.g., sugars such as xylose and glucose, sugar alcohols and other alcohols such as ethanol and butanol. Described herein are methods and systems for removing (e.g., filtering, destroying, diluting, converting) process gases, for example, ozone and VOCs, produced during biomass processing, e.g., during irradiation of the biomass with an electron beam.

Processes for manufacturing sugar solutions and products derived therefrom are described herein. These processes can include, for example, optionally mechanically treating a cellulosic and/or lignocellulosic feedstock. Before and/or after this treatment, the feedstock can be treated with another treatment, for example, irradiation, steam explosion, pyrolysis, sonication, chemical treatment (e.g., acid, base or solvents) and/or oxidation to reduce, or further reduce its recalcitrance. A sugar solution is formed by saccharifying the feedstock by, for example, the addition of one or more enzymes and/or one of more acids. A product can be derived from the sugar solution, for example, by fermentation to an alcohol or hydrogenation to a sugar alcohol. Further processing can include purifying the solution, for example, by distillation. If desired, the steps of measuring lignin content and setting or adjusting process parameters (e.g., irradiation dosage) based on this measurement can be performed at various stages of the process, for example, as described in U.S. Pat. No. 8,415,122 issued Apr. 9, 2013, the complete disclosure of which is incorporated herein by reference.

Since the recalcitrance reducing treatment step can be a high energy process, the treatment can be performed within an enclosure, e.g., a vault and/or bunker system to contain the energy and/or some of the products, e.g., process gases, derived from the energetic process, which could otherwise be hazardous. For example, the vault can be configured to contain heat energy, electrical energy (e.g., high voltages, electric discharges), radiation energy (e.g., X-rays, accelerated particles, gamma-rays, ultraviolet radiation), explosion energy (e.g., a shock wave, projectiles, blast wind), gases (e.g., ozone, steam, nitrogen oxides and/or volatile organic compounds) and combinations of these. Although this containment protects people and equipment outside of the vault, the equipment inside the vault is subjected to the energy and/or products derived from the energetic process. In some cases, this containment can exacerbate the negative effects, for example, by not allowing dissipation of gases and particulates (e.g., fines, dust, soot, carbon containing fine particles, ozone, steam, nitrogen oxides and/or volatile organic compounds). For example, many electron beam systems have delicate window structures that can be damaged by process gases or particulates. The deleterious effects of hazardous gases and particulates can be mitigated by diluting, removing converting and/or destroying any process gases and/or particulates.

If treatment methods for reducing the recalcitrance include irradiation of a feedstock (e.g., cellulosic or lignocellulosic feedstock or even hydrocarbon-containing feedstocks), for example, with ionizing radiation, ozone may be produced by the irradiation of oxygen (e.g., oxygen present in air). Oxides of nitrogen can also be produced by irradiation of air, as described in "Toxic Gas Production at Electron Linear Accelerators", W. P. Swanson, SLAC-PUB_2470, February 1980, the entire disclosure of which is incorporated herein by reference. The irradiation can also cause heating and decomposition of the biomass material that can release and/or produce VOCs, HAPs and carbon-containing particulates (e.g., soot). Ozone is a strong oxidant with a redox potential of 2.07 V (vs the Standard Hydrogen Electrode: SHE), higher than other known strong oxidants such as hydrogen peroxide, permanganate, chlorine gas and hypochlorite with redox potentials of 1.77 V, 1.67 V, 1.36 V and 0.94 V, respectively. Therefore, materials, for example, organic materials, are susceptible to degradation by ionizing radiation and oxidation by ozone. For example, the materials can degrade through chain scission, cross-linking, oxidation and heating. In addition, metal components are susceptible to oxidation and degradation by ozone causing them, for example, to corrode/pit and/or rust. Soot and VOCs can be hazardous and/or damaging to equipment, for example, posing a breathing hazard and/or coating and interfering with the operation of equipment. Soot can also damage delicate windows (e.g., window foils) utilized for electron extraction in irradiation devices.

Therefore, equipment that includes polymers and some metals (e.g., excluding perhaps corrosion resistant or noble metals) can be damaged. For example, damage can occur to belts that include organic material, for example, those used in equipment, e.g., as the coupling between a drive motor and an eccentric fly wheel of a vibratory conveyor. Systems and/or motor components that can be susceptible to damage by ozone and radiation include, for example, wheels, bearings, springs, shock absorbers, solenoids, actuators, switches, gears, axles, washers, adhesives, fasteners, bolts, nuts, screws, brackets, frames, pulleys, covers, vibration dampeners, sliders, filters, vents, pistons, fans, fan blades, wires, wire sheathing, valves, drive shafts, computer chips, microprocessors, circuit boards and cables. Some organic materials that can be degraded by ionizing radiation and ozone include thermoplastics and thermosets. For example, organic materials that can be susceptible to damage include phenolics (e.g., bakelite), fluorinated hydrocarbons (e.g., Teflon), thermoplastics, polyamides, polyesters, polyurethanes, rubbers (e.g., butyl rubber, chlorinated polyethylene, poly norbornene), polyethers, polyethylene (linear low density polyethylene, high density polyethylene), polystyrenes, polyvinyls (e.g., poly vinyl chloride), cellulosics, amino resins (e.g., urea formaldehyde), polyamines, polyamides, acrylics (e.g., methyl methacrylate), acetals (e.g., polyoxymethylene) lubricants (e.g., oils and gels), polysiloxanes and combinations of these.

FIG. 1 depicts an embodiment of the invention shown as a top perspective view. The view shows enclosing walls 110 (in the form of blocks) of a vault with doors 112 and foundation 113. In the particular embodiment shown, the walls are made of blocks, the walls having a thickness of approximately six feet. The ceiling/roof is not shown so the interior of the vault can be more clearly described. The view includes a high voltage (e.g., 1 MV) power source 120 and an electrical conduit 122 connecting the power source to the electron accelerator 124. In this embodiment, the electrical conduit 122 is a "pipe in a pipe" design with insulating gas, e.g., $SF_6$, between pipes. Distal (D) end of accelerator 124 has been leaded to prevent X-rays from emanating from the distal end of 124. The power source, electrical conduit and electron accelerator are supported by the concrete roof of the vault, outside the vault. The electron accelerator is connected to a scan horn 128 by a conduit 130 (high vacuum electron guide) that passes through the concrete ceiling (e.g., 4 to 6 feet thickness). A conveyor 132 is positioned for conveying biomass under the scan horn while the scan horn irradiates the biomass. A window cooling air conduit 140 brings air from outside the vault through the ceiling and is connected to a system 200 for blowing the cooling air across an electron extraction window, e.g., a titanium foil window. The vault also includes an air conduit 144 for removing the air and other gases, such as process gases (e.g., hazardous gases, HAPs, VOCs), from the interior of the vault to the exterior of the vault. Air conduit 144 is fed by air intake manifold 182 that can include vents (e.g., configured as a screen, grill or mesh), for example 184. Component 182 can include screens, filters and/or air flow controllers. Ideally manifold 182 does not significantly reduce the air flow. In some instances air flow into the vault is on the order of 1000 CFM and air flow out is on the order of 5000 CFM, which maintains a negative pressure inside the vault. In this embodiment, the outer perimeter of the vault can be about 34×34 feet and the ceiling height can be about 8 feet. The interior volume of the vault is therefore about 4600 cubic feet. The turnover rate of the atmosphere can be at least about 0.25 turnover per minute (e.g., at least about 0.5 turnovers, at least 1 turnover per minute, at least about 2 turnovers per minute, at least about 3 turnovers per minute, at least 4 turnovers per minute, at least 5 turnovers per minute, or between 1 and 5 turnovers per minute, between about 2 and 4 turnovers per minute). The turnover rate is the rate of gas exchange in the vault.

Construction materials can be chosen to increase the containment of processes gases in vault and improve the lifetime of the vault (e.g., by reducing corrosion). For example, the porosity of the walls can be reduced by infusion of materials into the construction blocks. For example, concrete with lower permeability can generally be achieved by substituting between 25 to 65 percent slag cement for Portland cement. Finely-divided solids (e.g., lime, silicates and colloidal silica) added to the cement when the blocks are made can reduce permeability to water and gases by increasing the density or by filling up voids. Some crystalline admixtures react with water and cement particles in the concrete to form calcium silicate hydrates and/or pore-blocking precipitates in the existing microcracks and capillaries. The resulting crystalline deposits, which are analogous to calcium silicate hydrate formation, become integrally bound with the hydrated pastes. Porosity reducing additives can also include hydrophobic water-repellent chemicals based on soaps and long-chain fatty acids derivatives, vegetable oils (tallows, soya-based materials, and greases), and petroleum (mineral oil, paraffin waxes, and bitumen emulsions). These materials are more useful for providing a water repellency layer on the material and would be more usefully applied to the exterior portions of the vault to aid in decreasing interior vault humidity, which can exacerbate corrosion in the vault. In addition, to improve the life of the structures, the interior surfaces (e.g., of concrete blocks) can be coated or covered with a corrosion resistant material, such as stainless steel.

Figure 2:
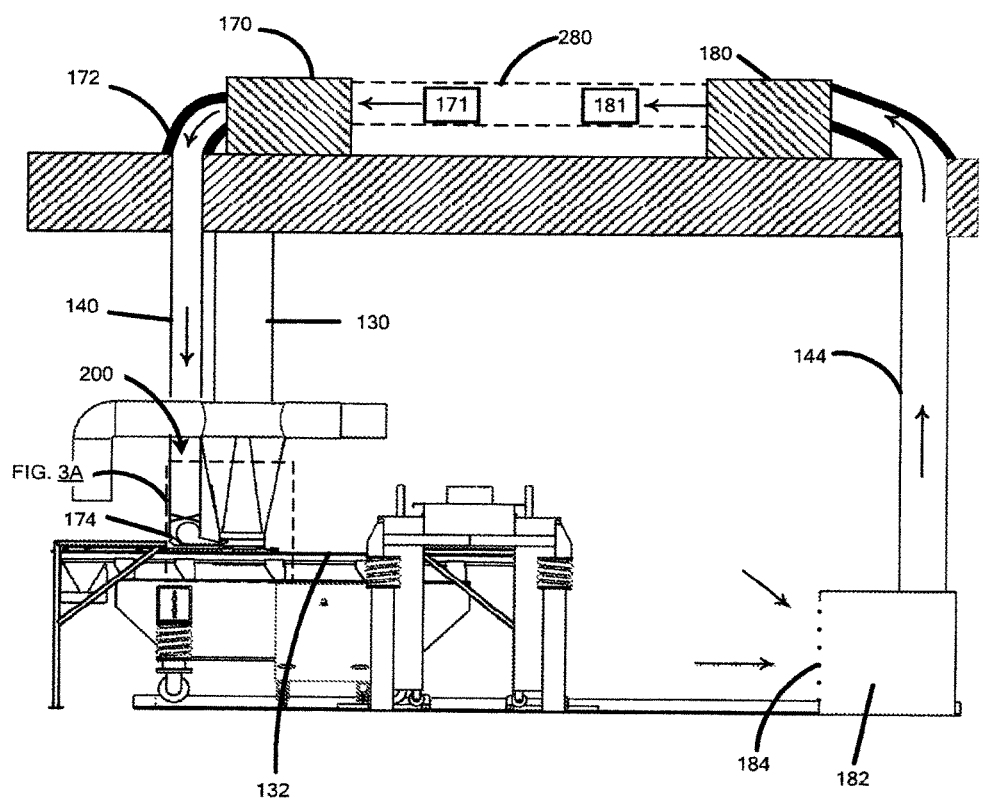
FIG. 2 is a side view of the gas mitigation system components shown in FIG. 1.

FIG. 2 is a right side view of the process gas (e.g., hazardous gas) mitigation system components some of which were introduced in FIG. 1. In FIG. 2 the vault walls, foundation, irradiator power source and electrical conduit for the power source are omitted for clarity. A blower system 170 blows air into the vault in the direction shown by the arrows. For example, air is shown on the left side of the drawing being blown from the outside of the vault 171, though a ceiling inlet 172 (which is often leaded), and down a conduit 140, to an air outlet inside the vault 174 that is an outlet of a window cooling system to be described in detail with reference to FIG. 3A. Therefore, an air flow path from outside the vault to the interior is provided through system 170, conduit 140, through the interior of the window cooling system (described with ref to FIGS. 3A and 3B), and outlet 174 for this embodiment. Other gas inlets into the vault can be utilized if desired, for example, to cool a product or equipment in the vault.

Air in the vault is extracted out of the vault in the directions shown by the arrows on the right side of the drawing. In particular, air is drawn through grills (e.g., screen, mesh) disposed on exhaust manifold 182 as previously described. System 180 includes fans/blowers, and or grills (e.g., screens, mesh) and/or air pumps for drawing air into manifold 182, up conduit 144, and out of the vault. The air is made to pass through a process case, such as an ozone destruction system, e.g., a carbon filter that destroys any process gas, such as ozone (converting it to oxygen) and adsorbs or destroys volatile organic compounds. The destruction system can be disposed anywhere in the flowing air path that passes through 182, 144 and 180 and before the air is vented to the atmosphere. In some embodiments, it is preferable to have destruction systems in manifold 182 so that venting pipe 144 is not exposed to process gases, e.g., ozone. In other embodiments it is preferred to have destructor systems located in system 180 and configured to be quickly replaced so that minimal or no down time is required for maintenance. In some cases the destructor systems (e.g., carbon filters) can be mounted to be automatically replaced when sensors indicated the need (e.g., ozone levels, VOCs and/or HAPs are higher than background levels). Vents on 180 (not shown), exhaust treated, e.g., de-ozonized, air into the atmosphere 181. Accordingly, this embodiment provides a gas, e.g., air, path from the interior of the vault to the exterior through a filtering (e.g., ozone and VOC filtering) system. In some embodiments the air inside the vault is recirculated. For example, an air conduit 280, depicted with dashed lines in FIG. 2, can optionally be added to the system to connect systems 170 and 180. In this way, purified air exiting system 180 could be recirculated through the vault via system 170 rather than being vented to the atmosphere. In some cases the vault can include one or more recirculating loops of gas.

Air pollution control technologies can be used for the destruction of process gases, for example, in manifold 182 and/or as part of system 180 or anywhere therebetween, e.g. in the flow path between 180 and 182. Thermal oxidation can be utilized for the destruction of, for example, HAPs and VOCs. Since some HAPs and all VOCs are carbon based, thermal oxidizer systems can be used to destroy these gases by complete oxidation to carbon dioxide and water. Some types of thermal oxidizer systems, for example, that can be utilized to treat the process gases as described herein, are regenerative thermal oxidizers, regenerative catalytic oxidizers, thermal recuperative oxidizers and direct fired thermal oxidizer. The first three thermal oxidizer systems can be preferable when designing for high energy efficiency because they all include some form of energy (e.g., heat) recovery and can have very high thermal efficiencies (e.g., greater than 95%). Air pollution control technologies for ozone generally include systems that convert ozone to oxygen. Other process gases, for example, $NO_x$ can also be treated with ammonia to produced nitrogen and water. Filtering or abatement systems for $SF_6$ gas can also be included in the systems to be included in some embodiments of the invention.

Air pollution technologies often utilize a metal or metal oxide catalyst. For example, metal and metal oxide catalysts (e.g., $CuO$—$MnO_2$, vanadium oxides, tungsten oxides, Pd and Pt). The catalysts allow the conversion reactions (e.g., to $CO_2$ and water, to $O_2$, to $N_2$ and water) to occur at relatively lower temperatures, for example, at temperatures as low as about 200 deg C. (e.g., 100 to 400 deg C.) lower than without the catalysts). Air pollution technologies also often utilize activated carbon. Ozone can be reduced to oxygen directly utilizing an activated carbon filter (e.g., bed, column). Activated carbons also act as an adsorbent for VOCs and HAPs, selectively removing and holding the gases on the surface until the carbon is regenerated. Activated carbons can be utilized in any useful form, for example, powdered carbon, granular carbon, extruded carbon, bead carbon, impregnated carbon (for example, impregnated with iodine, silver and metal ions, e.g., Al, Mn, Zn, Fe, Li, Ca metal ions), polymer coated carbon, polymer supported carbon, acid washed carbon, high purity carbon, aerogel carbon, carbon cloth and/or activated forms of these. The carbon can be designed/formed into different configurations, for example, as a web filter, a pleated filter, a spiral filter, a layered filter, a packed column filter, and combinations of these.

The catalysts and activated carbon as described herein can be utilized in an any useful configuration, e.g., pelletized, extruded, supported (e.g., on silica, on alumina, on carbon, on graphite, on aluminosilicates, on clays, on a foam, on a sponge, on a mesh, on beads, on a honeycomb structure, on a ceramic, on a woven or non-woven cloth, on a pleated filter, on a spiral filter, on a layered filter), as a mesh, as a wire, as fibers, in a column and/or on an filtering bed.

Optionally, process gases (e.g., components to be removed and/or destroyed in the gas) can be concentrated using, for example, a rotor concentrator and/or a centrifuge and then this concentrated gas stream can be treated with the pollution control systems described herein. Concentration can provide the advantage of not requiring a high throughput of gas through one of the air pollution control systems as described herein, so that a smaller capacity (e.g., lower gas flow) system can be utilized. Optionally, the process gas stream can be split into two or more flows and each flow treated independently.

The air pollution technologies and systems can be utilized in combinations and in any order to treat the process gases. For example, systems for destruction and/or removal of VOCs and HAPs can be utilized prior to ozone destruction systems. Additional systems can be utilized, for example, particulate filters, in combinations with these systems. Removal of particulates, then removal of VOCs and HAPs followed by Ozone removal can be preferred to reduce catalyst deactivation (e.g., fouling and catalyst poisoning can be reduced).

Some suppliers of process gas mitigation equipment (e.g., air pollution control technologies) and related supplies (e.g., filters, catalysts, activated carbon) include: Anguil Environmental Systems, Inc. (Milwaukee, Wis.); PureSphere Co., Inc. (Korea); General Air Products, Inc. (Exton, Pa.); Cabot Corp. (Boston, Mass.); Corporate Consulting Service Instruments, Inc. (Arkon, Ohio); Ozone Solutions, Inc. (Hull, Iowa); Columbus Industries, Inc. (Ashville, Ohio); California Carbon Co. Inc. (Wilmington, Calif.); Calgon Carbon Corporation (Pittsburgh, Pa.); and General Carbon Co. (Paterson, N.J.). Some specific ozone destructor units that can be utilized in the methods described herein are; the NT-400 unit available from Auguil Environmental Systems Inc. and/or scaled up versions of this unit. An exemplary ozone destructor system that can be utilized in manifold 182 is the NT-400 or a scaled up version of this system (e.g., so that high gas flow rates can be utilized), available from Ozone Solutions, Inc.

Figure 3A:
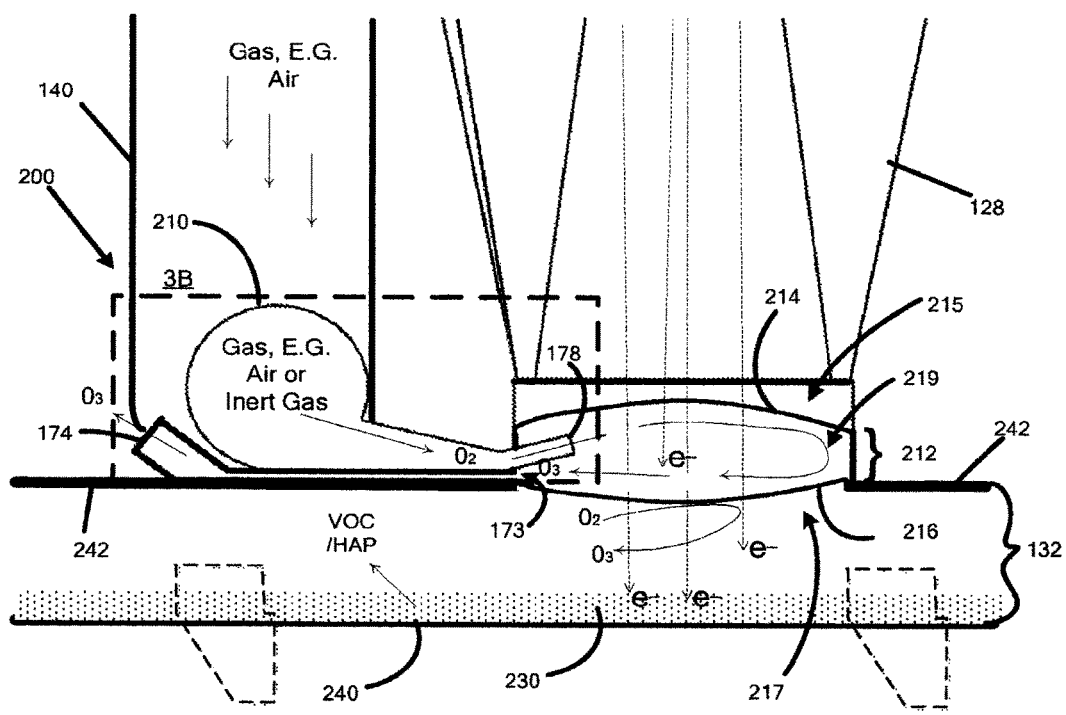
FIG. 3A is a detailed side view showing part of the gas mitigation system including a system for air cooling window foils.

FIG. 3A is a detailed side view showing part of the process gas mitigation system including a system 200 for air-cooling window foils. In this air-cooling system, air entering the vault through conduit 140 is blown through manifold 210 and directed into an enclosed area 212 through conduit 178. The enclosed area 212 is positioned between the scan horn 128 and a conveyor system 132, which includes a trough 240 for carrying biomass and a conveyor cover 242. The enclosed area 212 is defined on one side by one or more foils 214 (e.g., titanium foils) on the scanning horn, and on the other side by one or more foils 216 (e.g., a window including titanium foil) mounted to the edges of an opening on the conveyor cover 242. The foils on the scanning horn allow electrons from the high vacuum side 215 of the scanning horn to flow through the high pressure area between the foils 219 and to the atmospheric side 217, as indicated by the "e−" arrows in FIG. 3A. Outlet 174 (and/or gap 173 see FIG. 3B) is sized such that the pressure in the space 212 (high pressure area 219) is sufficient to keep the foils from fluttering in the air flows therein. For example, the pressure in 219 is higher than atmospheric pressure by at least about 0.1 psi, higher than atmospheric pressure by about 1 psi or from about 50-200 psig (e.g., about 75-200 psig, about 80-150 psig). Foil 216 protects foil 214 from implosion, such as if particulates are projected towards the electron extraction windows from the conveyor. For example, an outlet flow path, for example, the outlet 174 and/or gap 173, can have a minimum cross sectional area perpendicular to the flow path of the gas (e.g., air, nitrogen, argon, helium) out of the space 212 that less than about 10% (e.g., less than about 20% the area, less than about 30% the area, less than about 40% the area, less than about 50% the area, less than about 60% the area, less than about 70% the area, less than about 80% the area) the minimum cross sectional area of the flow path of the gas into the space 212 (e.g., through the opening of conduit 178). During biomass treatment, electrons pass from the vacuum side 215 of the scanning horn, through foil 214, through the high pressure area 219, through foil 216 and strike biomass 230 that is conveyed on conveyor surface (e.g., trough) 240. Heat is generated during these electron interactions, necessitating cooling of the foils. The flow of air from manifold 210 into the enclosed space assists with this cooling, maintaining efficient operation of the scanning head. For example, cooled window foils and window foils integrated with conveyors.

Figure 3B:
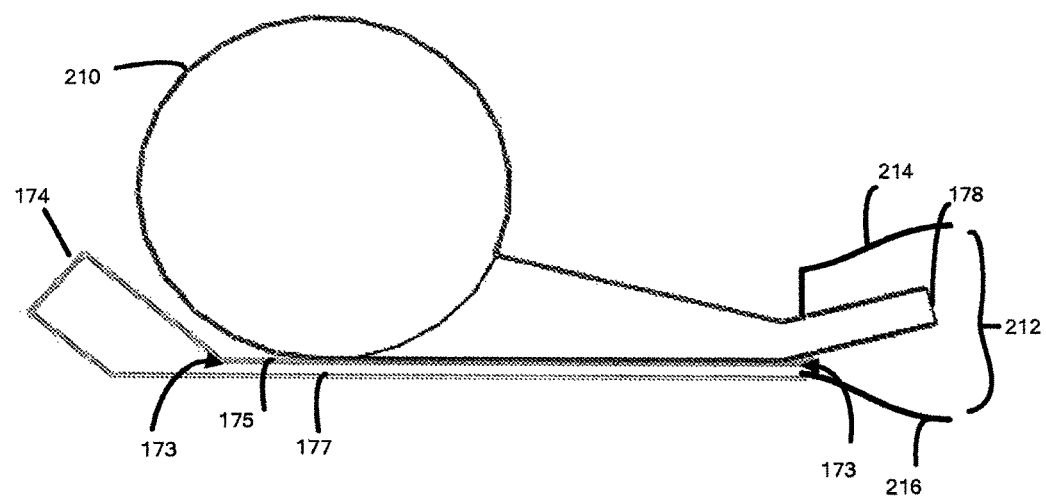
FIG. 3B is a highly enlarged detail view of area 3B in FIG. 3A.
Figure 3C:
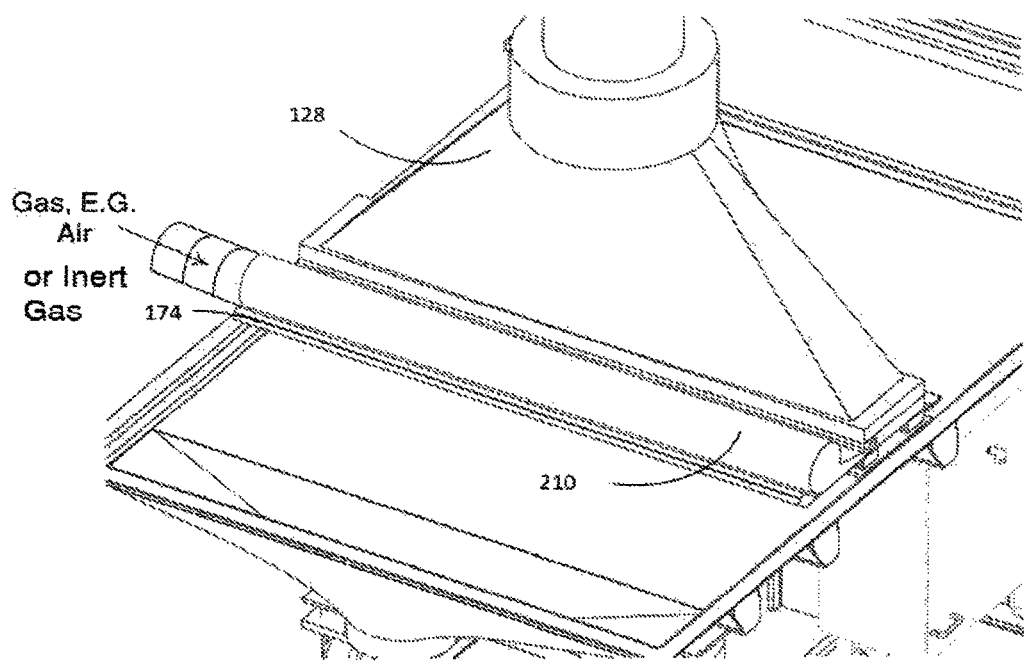
FIG. 3C is an enlarged detailed perspective view of the electron scanning horn, window cooling system and conveyor.

As discussed above, the electron interaction with the biomass can reduce the recalcitrance of the biomass. Energy dissipation processes due to the electrons striking the biomass or the conveyor surface can also occur. The heat produced, and/or the recalcitrance reduction of the biomass, can release (e.g., create, volatilize) volatile organic compounds (VOCs) and hazardous air pollutants (HAP), as indicated by the "VOC/HAP" arrow in FIG. 3A. Electrons can also interact with the components of air, for example, dioxygen, producing toxic gases, e.g., ozone. As shown in FIGS. 3A and 3B, ozone that is produced in the enclosed area 212 is vented out into the surrounding atmosphere, e.g., the vault, by way of the gap 173 (FIG. 3B) and through outlet 174. The gap 173 is defined by sheet (e.g., stainless steel sheet) 175 and sheet 177 that are part of window cooling system and mounted to the manifold 210. The gap 173 defines a conduit between the space 212 and the outlet 174. The outlet 174 and manifold 210 are in fluid communication through the enclosure 212. FIG. 3C is a perspective view showing of the scan horn, manifold 210 and outlet 174.

Some of the ozone generated during irradiation of biomass can react (e.g., oxidize) the biomass, while some of the ozone can leak out of the enclosed conveyor 132 into the vault. However, some ozone may be carried out of the vault with the biomass. To control the ozone that exits the vault with the biomass, an ozone abatement system can be used, e.g., a closed loop air conveyor with ozone abatement systems. For example, closed loop pneumatic conveyors and ozone abatement systems.

In some embodiments an inert gas, for example nitrogen, argon, carbon dioxide, He, $SF_6$, $SiF_4$, $CF_4$, or mixtures thereof (e.g., more than about 80% nitrogen, more than about 90% nitrogen, more than about 95% nitrogen, more than about 99% nitrogen), can be used to purge the vault. For example, with reference to FIG. 2 the inert gas is supplied to the vault through inlet 172. Processing the biomass in an atmosphere of inert gas, rather than air, can reduce or even eliminate the formation of ozone. An inert gas can be supplied by a tank, transported from a central location through a pipe and or generated close to the irradiation site. On site nitrogen generation technologies include membrane technology (e.g., hollow fiber membrane technology) and pressure swing adsorption technologies. The inert gas can be recycled, as described for other gases by drawing the vault atmosphere through manifold 182, through system 180 and then coupling the flows 181 and 171. Pressure adjustments and inert gas addition to compensate for any loss can be done by systems such as 170 and 180 in addition to attachment to an inert gas compensation source (e.g., tank, supply in fluid communication with 170 and/or 180). Since the inert gas avoids the production of ozone no ozone destruction unit is necessary in this optional embodiment.

In some embodiments the pressure inside the vault is slightly lower than the pressure outside the vault. Ideally, the vault would be airtight so that no process gases escape into the atmosphere, however this would in practice be difficult to achieve. Thus, a similar result can be achieved by making the active flow out of the vault, and through a process gas abatement system, be higher than the air/gas made to flow into the vault, e.g., using system 170 as discussed above. For example, the pressure in the vault can be at least about 0.001% lower than the pressure outside of the vault (e.g., at least about 0.002% lower, at least about 0.004% lower, at least about 0.006% lower, at least about 0.008% lower, at least about 0.01% lower, at least about 0.05% lower, at least about 0.1% lower, at least about 0.5% lower, at least about 1% lower, at least about 2% lower, at least about 5% lower, at least about 10% lower, at least about 50% lower, or at least about 100% lower). For example, if the pressure outside of the vault is 1 atm, and the pressure inside the vault is at least 0.1% lower than the pressure outside the vault, then the pressure inside the vault is at least 0.9 atm or lower. The pressure differences can be achieved by controlling flow rate of air and/or gases into and out of the vault. For example, referring to FIG. 2, by adjusting systems 170 and 180 so that the flow rate into the vault at 171 is at a lower rate than the flow rate out of the vault at 181. For example, the flow rate at an outlet to the vault, flowing air out of the vault, can be at least 0.1 times the flow rate at an inlet to the vault, flowing air into the vault (e.g., at least 0.5 times, at least 1 times, at least 2 times, at least 3 times, at least 4 times, at least 5 times, at least 10 times, at least 50 times, at least 100 times, or at least 200 times).

Some more details and reiterations of processes for treating a feedstock that can be utilized, for example, with the embodiments already discussed above, or in other embodiments, are described in the following disclosures.

Radiation Treatment

The feedstock can be treated with radiation to modify its structure to reduce its recalcitrance. Such treatment can, for example, reduce the average molecular weight of the feedstock, change the crystalline structure of the feedstock, and/or increase the surface area and/or porosity of the feedstock. Radiation can be by, for example, electron beam, ion beam, 100 nm to 280 nm ultraviolet (UV) light, gamma or X-ray radiation. Radiation treatments and systems for treatments are discussed in U.S. Pat. No. 8,142,620 and U.S. patent application Ser. No. 12/417,731, the entire disclosures of which are incorporated herein by reference.

Each form of radiation ionizes the biomass via particular interactions, as determined by the energy of the radiation. Heavy charged particles primarily ionize matter via Coulomb scattering; furthermore, these interactions produce energetic electrons that may further ionize matter. Alpha particles are identical to the nucleus of a helium atom and are produced by the alpha decay of various radioactive nuclei, such as isotopes of bismuth, polonium, astatine, radon, francium, radium, several actinides, such as actinium, thorium, uranium, neptunium, curium, californium, americium, and plutonium. Electrons interact via Coulomb scattering and bremsstrahlung radiation produced by changes in the velocity of electrons.

When particles are utilized, they can be neutral (uncharged), positively charged or negatively charged. When charged, the charged particles can bear a single positive or negative charge, or multiple charges, e.g., one, two, three or even four or more charges. In instances in which chain scission is desired to change the molecular structure of the carbohydrate containing material, positively charged particles may be desirable, in part, due to their acidic nature. When particles are utilized, the particles can have the mass of a resting electron, or greater, e.g., 500, 1000, 1500, or 2000 or more times the mass of a resting electron. For example, the particles can have a mass of from about 1 atomic unit to about 150 atomic units, e.g., from about 1 atomic unit to about 50 atomic units, or from about 1 to about 25, e.g., 1, 2, 3, 4, 5, 10, 12 or 15 atomic units.

Gamma radiation has the advantage of a significant penetration depth into a variety of material in the sample.

In embodiments in which the irradiating is performed with electromagnetic radiation, the electromagnetic radiation can have, e.g., energy per photon (in electron volts) of greater than $10^2$ eV, e.g., greater than $10^3$, $10^4$, $10^5$, $10^6$, or even greater than $10^7$ eV. In some embodiments, the electromagnetic radiation has energy per photon of between $10^4$ and $10^7$, e.g., between $10^5$ and $10^6$ eV. The electromagnetic radiation can have a frequency of, e.g., greater than $10^{16}$ Hz, greater than $10^{17}$ Hz, $10^{18}$, $10^{19}$, $10^{20}$, or even greater than $10^{21}$ Hz. In some embodiments, the electromagnetic radiation has a frequency of between $10^{18}$ and $10^{22}$ Hz, e.g., between $10^{19}$ to $10^{21}$ Hz.

Electron bombardment may be performed using an electron beam device that has a nominal energy of less than 10 MeV, e.g., less than 7 MeV, less than 5 MeV, or less than 2 MeV, e.g., from about 0.5 to 1.5 MeV, from about 0.8 to 1.8 MeV, or from about 0.7 to 1 MeV. In some implementations the nominal energy is about 500 to 800 keV.

The electron beam may have a relatively high total beam power (the combined beam power of all accelerating heads, or, if multiple accelerators are used, of all accelerators and all heads), e.g., at least 25 kW, e.g., at least 30, 40, 50, 60, 65, 70, 80, 100, 125, or 150 kW. In some cases, the power is even as high as 500 kW, 750 kW, or even 1000 kW or more. In some cases the electron beam has a beam power of 1200 kW or more, e.g., 1400, 1600, 1800, or even 3000 kW.

This high total beam power is usually achieved by utilizing multiple accelerating heads. For example, the electron beam device may include two, four, or more accelerating heads. The use of multiple heads, each of which has a relatively low beam power, prevents excessive temperature rise in the material, thereby preventing burning of the material, and also increases the uniformity of the dose through the thickness of the layer of material.

It is generally preferred that the bed of biomass material has a relatively uniform thickness. In some embodiments the thickness is less than about 1 inch (e.g., less than about 0.75 inches, less than about 0.5 inches, less than about 0.25 inches, less than about 0.1 inches, between about 0.1 and 1 inch, between about 0.2 and 0.3 inches).

It is desirable to treat the material as quickly as possible. In general, it is preferred that treatment be performed at a dose rate of greater than about 0.25 Mrad per second, e.g., greater than about 0.5, 0.75, 1, 1.5, 2, 5, 7, 10, 12, 15, or even greater than about 20 Mrad per second, e.g., about 0.25 to 2 Mrad per second. Higher dose rates allow a higher throughput for a target (e.g., the desired) dose. Higher dose rates generally require higher line speeds, to avoid thermal decomposition of the material. In one implementation, the accelerator is set for 3 MeV, 50 mA beam current, and the line speed is 24 feet/minute, for a sample thickness of about 20 mm (e.g., comminuted corn cob material with a bulk density of 0.5 g/cm$^3$).

In some embodiments, electron bombardment is performed until the material receives a total dose of at least 0.1 Mrad, 0.25 Mrad, 1 Mrad, 5 Mrad, e.g., at least 10, 20, 30 or at least 40 Mrad. In some embodiments, the treatment is performed until the material receives a dose of from about 10 Mrad to about 50 Mrad, e.g., from about 20 Mrad to about 40 Mrad, or from about 25 Mrad to about 30 Mrad. In some implementations, a total dose of 25 to 35 Mrad is preferred, applied ideally over a couple of passes, e.g., at 5 Mrad/pass with each pass being applied for about one second. Cooling methods, systems and equipment can be used before, during, after and in between radiations, for example, utilizing a cooling screw conveyor and/or a cooled vibratory conveyor.

Using multiple heads as discussed above, the material can be treated in multiple passes, for example, two passes at 10 to 20 Mrad/pass, e.g., 12 to 18 Mrad/pass, separated by a few seconds of cool-down, or three passes of 7 to 12 Mrad/pass, e.g., 5 to 20 Mrad/pass, 10 to 40 Mrad/pass, 9 to 11 Mrad/pass. As discussed herein, treating the material with several relatively low doses, rather than one high dose, tends to prevent overheating of the material and also increases dose uniformity through the thickness of the material. In some implementations, the material is stirred or otherwise mixed during or after each pass and then smoothed into a uniform layer again before the next pass, to further enhance treatment uniformity.

In some embodiments, electrons are accelerated to, for example, a speed of greater than 75 percent of the speed of light, e.g., greater than 85, 90, 95, or 99 percent of the speed of light.

In some embodiments, any processing described herein occurs on lignocellulosic material that remains dry as acquired or that has been dried, e.g., using heat and/or reduced pressure. For example, in some embodiments, the cellulosic and/or lignocellulosic material has less than about 25 wt. % retained water, measured at 25° C. and at fifty percent relative humidity (e.g., less than about 20 wt. %, less than about 15 wt. %, less than about 14 wt. %, less than about 13 wt. %, less than about 12 wt. %, less than about 10 wt. %, less than about 9 wt. %, less than about 8 wt. %, less than about 7 wt. %, less than about 6 wt. %, less than about 5 wt. %, less than about 4 wt. %, less than about 3 wt. %, less than about 2 wt. %, less than about 1 wt. %, or less than about 0.5 wt. %.

In some embodiments, two or more ionizing sources can be used, such as two or more electron sources. For example, samples can be treated, in any order, with a beam of electrons, followed by gamma radiation and UV light having wavelengths from about 100 nm to about 280 nm. In some embodiments, samples are treated with three ionizing radiation sources, such as a beam of electrons, gamma radiation, and energetic UV light. The biomass is conveyed through the treatment zone where it can be bombarded with electrons.

It may be advantageous to repeat the treatment to more thoroughly reduce the recalcitrance of the biomass and/or further modify the biomass. In particular the process parameters can be adjusted after a first (e.g., second, third, fourth or more) pass depending on the recalcitrance of the material. In some embodiments, a conveyor can be used which includes a circular system where the biomass is conveyed multiple times through the various processes described above. In some other embodiments multiple treatment devices (e.g., electron beam generators) are used to treat the biomass multiple (e.g., 2, 3, 4 or more) times. In yet other embodiments, a single electron beam generator may be the source of multiple beams (e.g., 2, 3, 4 or more beams) that can be used for treatment of the biomass.

The effectiveness in changing the molecular/supermolecular structure and/or reducing the recalcitrance of the carbohydrate-containing biomass depends on the electron energy used and the dose applied, while exposure time depends on the power and dose. In some embodiments, the dose rate and total dose are adjusted so as not to destroy (e.g., char or burn) the biomass material. For example, the carbohydrates should not be damaged in the processing so that they can be released from the biomass intact, e.g. as monomeric sugars.

In some embodiments, the treatment (with any electron source or a combination of sources) is performed until the material receives a dose of at least about 0.05 Mrad, e.g., at least about 0.1, 0.25, 0.5, 0.75, 1.0, 2.5, 5.0, 7.5, 10.0, 15, 20, 25, 30, 40, 50, 60, 70, 80, 90, 100, 125, 150, 175, or 200 Mrad. In some embodiments, the treatment is performed until the material receives a dose of between 0.1-100 Mrad, 1-200, 5-200, 10-200, 5-150, 50-150 Mrad, 5-100, 5-50, 5-40, 10-50, 10-75, 15-50, 20-35 Mrad.

In some embodiments, relatively low doses of radiation are utilized, e.g., to increase the molecular weight of a cellulosic or lignocellulosic material (with any radiation source or a combination of sources described herein). For example, a dose of at least about 0.05 Mrad, e.g., at least about 0.1 Mrad or at least about 0.25, 0.5, 0.75. 1.0, 1.5, 2.0, 2.5, 3.0, 3.5, 4.0, or at least about 5.0 Mrad. In some embodiments, the irradiation is performed until the material receives a dose of between 0.1 Mrad and 2.0 Mrad, e.g., between 0.5 Mrad and 4.0 Mrad or between 1.0 Mrad and 3.0 Mrad.

It also can be desirable to irradiate from multiple directions, simultaneously or sequentially, in order to achieve a desired degree of penetration of radiation into the material. For example, depending on the density and moisture content of the material, such as wood, and the type of radiation source used (e.g., gamma or electron beam), the maximum penetration of radiation into the material may be only about 0.75 inch. In such a cases, a thicker section (up to 1.5 inch) can be irradiated by first irradiating the material from one side, and then turning the material over and irradiating from the other side. Irradiation from multiple directions can be particularly useful with electron beam radiation, which irradiates faster than gamma radiation but typically does not achieve as great a penetration depth.

Radiation Opaque Materials

As previously discussed, the invention can include processing the material in a vault and/or bunker that is constructed using radiation opaque materials. In some implementations, the radiation opaque materials are selected to be capable of shielding the components from X-rays with high energy (short wavelength), which can penetrate many materials. One important factor in designing a radiation shielding enclosure is the attenuation length of the materials used, which will determine the required thickness for a particular material, blend of materials, or layered structure. The attenuation length is the penetration distance at which the radiation is reduced to approximately 1/e (e=Euler's number) times that of the incident radiation. Although virtually all materials are radiation opaque if thick enough, materials containing a high compositional percentage (e.g., density) of elements that have a high Z value (atomic number) have a shorter radiation attenuation length and thus if such materials are used a thinner, lighter shielding can be provided. Examples of high Z value materials that are used in radiation shielding are tantalum and lead. Another important parameter in radiation shielding is the halving distance, which is the thickness of a particular material that will reduce gamma ray intensity by 50%. As an example for X-ray radiation with an energy of 0.1 MeV the halving thickness is about 15.1 mm for concrete and about 2.7 mm for lead, while with an X-ray energy of 1 MeV the halving thickness for concrete is about 44.45 mm and for lead is about 7.9 mm. Radiation opaque materials can be materials that are thick or thin so long as they can reduce the radiation that passes through to the other side. Thus, if it is desired that a particular enclosure have a low wall thickness, e.g., for light weight or due to size constraints, the material chosen should have a sufficient Z value and/or attenuation length so that its halving length is less than or equal to the desired wall thickness of the enclosure.

In some cases, the radiation opaque material may be a layered material, for example having a layer of a higher Z value material, to provide good shielding, and a layer of a lower Z value material to provide other properties (e.g., structural integrity, impact resistance, etc.). In some cases, the layered material may be a "graded-Z" laminate, e.g., including a laminate in which the layers provide a gradient from high-Z through successively lower-Z elements. In some cases the radiation opaque materials can be interlocking blocks, for example, lead and/or concrete blocks can be supplied by NELCO Worldwide (Burlington, Mass.), and reconfigurable vaults can be utilized.

A radiation opaque material can reduce the radiation passing through a structure (e.g., a wall, door, ceiling, enclosure, a series of these or combinations of these) formed of the material by about at least about 10%, (e.g., at least about 20%, at least about 30%, at least about 40%, at least about 50%, at least about 60%, at least about 70%, at least about 80%, at least about 90%, at least about 95%, at least about 96%, at least about 97%, at least about 98%, at least about 99%, at least about 99.9%, at least about 99.99%, at least about 99.999%) as compared to the incident radiation. Therefore, an enclosure made of a radiation opaque material can reduce the exposure of equipment/system/components by the same amount. Radiation opaque materials can include stainless steel, metals with Z values above 25 (e.g., lead, iron), concrete, dirt, sand and combinations thereof. Radiation opaque materials can include a barrier in the direction of the incident radiation of at least about 1 mm (e.g., 5 mm, 10 mm, 5 cm, 10 cm, 100 cm, 1 m and even at least 10 m).

Radiation Sources

The type of radiation determines the kinds of radiation sources used as well as the radiation devices and associated equipment. The methods, systems and equipment described herein, for example, for treating materials with radiation, can utilized sources as described herein as well as any other useful source.

Sources of gamma rays include radioactive nuclei, such as isotopes of cobalt, calcium, technetium, chromium, gallium, indium, iodine, iron, krypton, samarium, selenium, sodium, thallium, and xenon.

Sources of X-rays include electron beam collision with metal targets, such as tungsten or molybdenum or alloys, or compact light sources, such as those produced commercially by Lyncean.

Alpha particles are identical to the nucleus of a helium atom and are produced by the alpha decay of various radioactive nuclei, such as isotopes of bismuth, polonium, astatine, radon, francium, radium, several actinides, such as actinium, thorium, uranium, *neptunium*, curium, californium, americium, and plutonium.

Sources for ultraviolet radiation include deuterium or cadmium lamps.

Sources for infrared radiation include sapphire, zinc, or selenide window ceramic lamps.

Sources for microwaves include klystrons, Slevin type RF sources, or atom beam sources that employ hydrogen, oxygen, or nitrogen gases.

Accelerators used to accelerate the particles (e.g., electrons or ions) can be DC (e.g., electrostatic DC or electrodynamic DC), RF linear, magnetic induction linear or continuous wave. For example, various irradiating devices may be used in the methods disclosed herein, including field ionization sources, electrostatic ion separators, field ionization generators, thermionic emission sources, microwave discharge ion sources, recirculating or static accelerators, dynamic linear accelerators, van de Graaff accelerators, Cockroft Walton accelerators (e.g., PELLETRON® accelerators), LINACS, Dynamitrons (e.g., DYNAMITRON® accelerators), cyclotrons, synchrotrons, betatrons, transformer-type accelerators, microtrons, plasma generators, cascade accelerators, and folded tandem accelerators. For example, cyclotron type accelerators are available from IBA, Belgium, such as the RHODOTRON™ system, while DC type accelerators are available from RDI, now IBA Industrial, such as the DYNAMITRON®. Other suitable accelerator systems include, for example: DC insulated core transformer (ICT) type systems, available from Nissin High Voltage, Japan; S-band LINACs, available from L3-PSD (USA), Linac Systems (France), Mevex (Canada), and Mitsubishi Heavy Industries (Japan); L-band LINACs, available from Iotron Industries (Canada); and ILU-based accelerators, available from Budker Laboratories (Russia). Ions and ion accelerators are discussed in Introductory Nuclear Physics, Kenneth S. Krane, John Wiley & Sons, Inc. (1988), Krsto Prelec, FIZIKA B 6 (1997) 4, 177-206, Chu, William T., "Overview of Light-Ion Beam Therapy", Columbus-Ohio, ICRU-IAEA Meeting, 18-20 Mar. 2006, Iwata, Y. et al., "Alternating-Phase-Focused IH-DTL for Heavy-Ion Medical Accelerators", Proceedings of EPAC 2006, Edinburgh, Scotland, and Leitner, C. M. et al., "Status of the Superconducting ECR Ion Source Venus", Proceedings of EPAC 2000, Vienna, Austria. Some particle accelerators and their uses are disclosed, for example, in U.S. Pat. No. 7,931,784 to Medoff, the complete disclosure of which is incorporated herein by reference.

Electrons may be produced by radioactive nuclei that undergo beta decay, such as isotopes of iodine, cesium, technetium, and iridium. Alternatively, an electron gun can be used as an electron source via thermionic emission and accelerated through an accelerating potential. An electron gun generates electrons, which are then accelerated through a large potential (e.g., greater than about 500 thousand, greater than about 1 million, greater than about 2 million, greater than about 5 million, greater than about 6 million, greater than about 7 million, greater than about 8 million, greater than about 9 million, or even greater than 10 million volts) and then scanned magnetically in the x-y plane, where the electrons are initially accelerated in the z direction down the accelerator tube and extracted through a foil window. Scanning the electron beams is useful for increasing the irradiation surface when irradiating materials, e.g., a biomass, that is conveyed through the scanned beam. Scanning the electron beam also distributes the thermal load homogenously on the window and helps reduce the foil window rupture due to local heating by the electron beam. Window foil rupture is a cause of significant down-time due to subsequent necessary repairs and re-starting the electron gun.

Various other irradiating devices may be used in the methods disclosed herein, including field ionization sources, electrostatic ion separators, field ionization generators, thermionic emission sources, microwave discharge ion sources, recirculating or static accelerators, dynamic linear accelerators, van de Graaff accelerators, and folded tandem accelerators. Such devices are disclosed, for example, in U.S. Pat. No. 7,931,784 to Medoff, the complete disclosure of which is incorporated herein by reference.

A beam of electrons can be used as the radiation source. A beam of electrons has the advantages of high dose rates (e.g., 1, 5, or even 10 Mrad per second), high throughput, less containment, and less confinement equipment. Electron beams can also have high electrical efficiency (e.g., 80%), allowing for lower energy usage relative to other radiation methods, which can translate into a lower cost of operation and lower greenhouse gas emissions corresponding to the smaller amount of energy used. Electron beams can be generated, e.g., by electrostatic generators, cascade generators, transformer generators, low energy accelerators with a scanning system, low energy accelerators with a linear cathode, linear accelerators, and pulsed accelerators.

Electrons can also be more efficient at causing changes in the molecular structure of carbohydrate-containing materials, for example, by the mechanism of chain scission. In addition, electrons having energies of 0.5-10 MeV can penetrate low density materials, such as the biomass materials described herein, e.g., materials having a bulk density of less than 0.5 g/cm$^3$, and a depth of 0.3-10 cm. Electrons as an ionizing radiation source can be useful, e.g., for relatively thin piles, layers or beds of materials, e.g., less than about 0.5 inch, e.g., less than about 0.4 inch, 0.3 inch, 0.25 inch, or less than about 0.1 inch. In some embodiments, the energy of each electron of the electron beam is from about 0.3 MeV to about 2.0 MeV (million electron volts), e.g., from about 0.5 MeV to about 1.5 MeV, or from about 0.7 MeV to about 1.25 MeV. Methods of irradiating materials are discussed in U.S. Pat. App. Pub. 2012/0100577 A1, filed Oct. 18, 2011, the entire disclosure of which is herein incorporated by reference.

Electron beam irradiation devices may be procured commercially or built. For example, elements or components such inductors, capacitors, casings, power sources, cables, wiring, voltage control systems, current control elements, insulating material, microcontrollers and cooling equipment can be purchased and assembled into a device. Optionally, a commercial device can be modified and/or adapted. For example, devices and components can be purchased from any of the commercial sources described herein including Ion Beam Applications (Louvain-la-Neuve, Belgium), Wasik Associates Inc. (Dracut, Mass.), NHV Corporation (Japan), the Titan Corporation (San Diego, Calif.), Vivirad High Voltage Corp (Billerica, Mass.) and/or Budker Laboratories (Russia). Typical electron energies can be 0.5 MeV, 1 MeV, 2 MeV, 4.5 MeV, 7.5 MeV, or 10 MeV. Typical electron beam irradiation device power can be 1 kW, 5 kW, 10 kW, 20 kW, 50 kW, 60 kW, 70 kW, 80 kW, 90 kW, 100 kW, 125 kW, 150 kW, 175 kW, 200 kW, 250 kW, 300 kW, 350 kW, 400 kW, 450 kW, 500 kW, 600 kW, 700 kW, 800 kW, 900 kW or even 1000 kW. Accelerators that can be used include NHV irradiators medium energy series EPS-500 (e.g., 500 kV accelerator voltage and 65, 100 or 150 mA beam current), EPS-800 (e.g., 800 kV accelerator voltage and 65 or 100 mA beam current), or EPS-1000 (e.g., 1000 kV accelerator voltage and 65 or 100 mA beam current). Also, accelerators from NHV's high energy series can be used such as EPS-1500 (e.g., 1500 kV accelerator voltage and 65 mA beam current), EPS-2000 (e.g., 2000 kV accelerator voltage and 50 mA beam current), EPS-3000 (e.g., 3000 kV accelerator voltage and 50 mA beam current) and EPS-5000 (e.g., 5000 and 30 mA beam current). Tradeoffs in considering electron beam irradiation device power specifications include cost to operate, capital costs, depreciation, and device footprint. Tradeoffs in considering exposure dose levels of electron beam irradiation would be energy costs and environment, safety, and health (ESH) concerns. Typically, generators are housed in a vault, e.g., of lead or concrete, especially for production from X-rays that are generated in the process. Tradeoffs in considering electron energies include energy costs.

The electron beam irradiation device can produce either a fixed beam or a scanning beam. A scanning beam may be advantageous with large scan sweep length and high scan speeds, as this would effectively replace a large, fixed beam width. Further, available sweep widths of 0.5 m, 1 m, 2 m or more are available. The scanning beam is preferred in most embodiments described herein because of the larger scan width and reduced possibility of local heating and failure of the windows.

Electron Guns—Windows

The extraction system for an electron accelerator can include two window foils. The cooling gas in the two foil window extraction system can be a purge gas or a mixture, for example, air, or a pure gas. In one embodiment, the gas is an inert gas such as nitrogen, argon, helium and/or carbon dioxide. It is preferred to use a gas rather than a liquid since energy losses to the electron beam are minimized. Mixtures of pure gas can also be used, either pre-mixed or mixed in line prior to impinging on the windows or in the space between the windows. The cooling gas can be cooled, for example, by using a heat exchange system (e.g., a chiller) and/or by using boil off from a condensed gas (e.g., liquid nitrogen, liquid helium). Window foils are described in PCT/US2013/64332 filed Oct. 10, 2013 the full disclosure of which is incorporated by reference herein.

Heating and Throughput During Radiation Treatment

Several processes can occur in biomass when electrons from an electron beam interact with matter in inelastic collisions. For example, ionization of the material, chain scission of polymers in the material, cross linking of polymers in the material, oxidation of the material, generation of X-rays ("Bremsstrahlung") and vibrational excitation of molecules (e.g., phonon generation). Without being bound to a particular mechanism, the reduction in recalcitrance can be due to several of these inelastic collision effects, for example, ionization, chain scission of polymers, oxidation and phonon generation. Some of the effects (e.g., especially X-ray generation), necessitate shielding and engineering barriers, for example, enclosing the irradiation processes in a concrete (or other radiation opaque material) vault. Another effect of irradiation, vibrational excitation, is equivalent to heating up the sample. Heating the sample by irradiation can help in recalcitrance reduction, but excessive heating can destroy the material, as will be explained below.

The adiabatic temperature rise ($\Delta T$) from adsorption of ionizing radiation is given by the equation: $\Delta T = D/C_p$: where D is the average dose in kGy, $C_p$ is the heat capacity in J/g ° C., and $\Delta T$ is the change in temperature in ° C. A typical dry biomass material will have a heat capacity close to 2. Wet biomass will have a higher heat capacity dependent on the amount of water since the heat capacity of water is very high (4.19 J/g ° C.). Metals have much lower heat capacities, for example 304 stainless steel has a heat capacity of 0.5 J/g ° C. The temperature change due to the instant adsorption of radiation in a biomass and stainless steel for various doses of radiation is shown in Table 1. At the higher temperatures biomass will decompose causing extreme deviation from the estimated changes in temperature.

TABLE 1

Calculated Temperature increase for biomass and stainless steel.

| Dose (Mrad) | Estimated Biomass ΔT (° C.) | Steel ΔT (° C.) |
|---|---|---|
| 10 | 50 | 200 |
| 50 | 250 (decomposed) | 1000 |
| 100 | 500 (decomposed) | 2000 |
| 150 | 750 (decomposed) | 3000 |
| 200 | 1000 (decomposed) | 4000 |

High temperatures can destroy and/or modify the biopolymers in biomass so that the polymers (e.g., cellulose) are unsuitable for further processing. A biomass subjected to high temperatures can become dark, sticky and give off odors indicating decomposition. The stickiness can even make the material hard to convey. The odors can be unpleasant and be a safety issue. In fact, keeping the biomass below about 200° C. has been found to be beneficial in the processes described herein (e.g., below about 190° C., below about 180° C., below about 170° C., below about 160° C., below about 150° C., below about 140° C., below about 130° C., below about 120° C., below about 110° C., between about 60° C. and 180° C., between about 60° C. and 160° C., between about 60° C. and 150° C., between about 60° C. and 140° C., between about 60° C. and 130° C., between about 60° C. and 120° C., between about 80° C. and 180° C., between about 100° C. and 180° C., between about 120° C. and 180° C., between about 140° C. and 180° C., between about 160° C. and 180° C., between about 100° C. and 140° C., between about 80° C. and 120° C.).

It has been found that irradiation above about 10 Mrad is desirable for the processes described herein (e.g., reduction of recalcitrance). A high throughput is also desirable so that the irradiation does not become a bottle neck in processing the biomass. The treatment is governed by a Dose rate equation: M=FP/D·time, where M is the mass of irradiated material (kg), F is the fraction of power that is adsorbed (unit less), P is the emitted power (kW=Voltage in MeV×Current in mA), time is the treatment time (sec) and D is the adsorbed dose (kGy). In an exemplary process where the fraction of adsorbed power is fixed, the Power emitted is constant and a set dosage is desired, the throughput (e.g., M, the biomass processed) can be increased by increasing the irradiation time. However, increasing the irradiation time without allowing the material to cool, can excessively heat the material as exemplified by the calculations shown above. Since biomass has a low thermal conductivity (less than about 0.1 Wm$^{-1}$K$^{-1}$), heat dissipation is slow, unlike, for example, metals (greater than about 10 Wm$^{-1}$K$^{-1}$) which can dissipate energy quickly as long as there is a heat sink to transfer the energy to.

Electron Guns—Beam Stops

In some embodiments the systems and methods include a beam stop (e.g., a shutter). For example, the beam stop can be used to quickly stop or reduce the irradiation of material without powering down the electron beam device. Alternatively the beam stop can be used while powering up the electron beam, e.g., the beam stop can stop the electron beam until a beam current of a desired level is achieved. The beam stop can be placed between the primary foil window and a secondary foil window. For example, the beam stop can be mounted so that it is movable, that is, so that it can be moved into and out of the beam path. Even partial coverage of the beam can be used, for example, to control the dose of irradiation. The beam stop can be mounted to the floor, to a conveyor for the biomass, to a wall, to the radiation device (e.g., at the scan horn), or to any structural support. Preferably the beam stop is fixed in relation to the scan horn so that the beam can be effectively controlled by the beam stop. The beam stop can incorporate a hinge, a rail, wheels, slots, or other means allowing for its operation in moving into and out of the beam. The beam stop can be made of any material that will stop at least 5% of the electrons, e.g., at least 10%, 20%, 30%, 40%, 50%, 60%, 70%, at least 80%, 85%, 90%, 91%, 92%, 93%, 94%, 95%, 96%, 97%, 98%, 99% or even about 100% of the electrons.

The beam stop can be made of a metal including, but not limited to, stainless steel, lead, iron, molybdenum, silver, gold, titanium, aluminum, tin, or alloys of these, or laminates (layered materials) made with such metals (e.g., metal-coated ceramic, metal-coated polymer, metal-coated composite, multilayered metal materials).

The beam stop can be cooled, for example, with a cooling fluid such as an aqueous solution or a gas. The beam stop can be partially or completely hollow, for example, with cavities. Interior spaces of the beam stop can be used for cooling fluids and gases. The beam stop can be of any shape, including flat, curved, round, oval, square, rectangular, beveled and wedged shapes.

The beam stop can have perforations so as to allow some electrons through, thus controlling (e.g., reducing) the levels of radiation across the whole area of the window, or in specific regions of the window. The beam stop can be a mesh formed, for example, from fibers or wires. Multiple beam stops can be used, together or independently, to control the irradiation. The beam stop can be remotely controlled, e.g., by radio signal or hard wired to a motor for moving the beam into or out of position.

Beam Dumps

The embodiments disclosed herein can also include a beam dump when utilizing a radiation treatment. A beam dump's purpose is to safely absorb a beam of charged particles. Like a beam stop, a beam dump can be used to block the beam of charged particles. However, a beam dump is much more robust than a beam stop, and is intended to block the full power of the electron beam for an extended period of time. They are often used to block the beam as the accelerator is powering up.

Beam dumps are also designed to accommodate the heat generated by such beams, and are usually made from materials such as copper, aluminum, carbon, beryllium, tungsten, or mercury. Beam dumps can be cooled, for example, using a cooling fluid that can be in thermal contact with the beam dump.

Biomass Materials

Lignocellulosic materials include, but are not limited to, wood, particle board, forestry wastes (e.g., sawdust, aspen wood, wood chips), grasses, (e.g., switchgrass, miscanthus, cord grass, reed canary grass), grain residues, (e.g., rice hulls, oat hulls, wheat chaff, barley hulls), agricultural waste (e.g., silage, canola straw, wheat straw, barley straw, oat straw, rice straw, jute, hemp, flax, bamboo, sisal, abaca, corn cobs, corn stover, soybean stover, corn fiber, alfalfa, hay, coconut hair), sugar processing residues (e.g., bagasse, beet pulp, agave bagasse), algae, seaweed, manure, sewage, and mixtures of any of these.

In some cases, the lignocellulosic material includes corncobs. Ground or hammermilled corncobs can be spread in a layer of relatively uniform thickness for irradiation, and after irradiation are easy to disperse in the medium for further processing. To facilitate harvest and collection, in some cases the entire corn plant is used, including the corn stalk, corn kernels, and in some cases even the root system of the plant.

Advantageously, no additional nutrients (other than a nitrogen source, e.g., urea or ammonia) are required during fermentation of corncobs or cellulosic or lignocellulosic materials containing significant amounts of corncobs.

Corncobs, before and after comminution, are also easier to convey and disperse, and have a lesser tendency to form explosive mixtures in air than other cellulosic or lignocellulosic materials such as hay and grasses.

Cellulosic materials include, for example, paper, paper products, paper waste, paper pulp, pigmented papers, loaded papers, coated papers, filled papers, magazines, printed matter (e.g., books, catalogs, manuals, labels, calendars, greeting cards, brochures, prospectuses, newsprint), printer paper, polycoated paper, card stock, cardboard, paperboard, materials having a high α-cellulose content such as cotton, and mixtures of any of these. For example, paper products as described in U.S. application Ser. No. 13/396,365 ("Magazine Feedstocks" by Medoff et al., filed Feb. 14, 2012), the full disclosure of which is incorporated herein by reference.

Cellulosic materials can also include lignocellulosic materials which have been partially or fully de-lignified.

In some instances other biomass materials can be utilized, for example, starchy materials. Starchy materials include starch itself, e.g., corn starch, wheat starch, potato starch or rice starch, a derivative of starch, or a material that includes starch, such as an edible food product or a crop. For example, the starchy material can be arracacha, buckwheat, banana, barley, cassava, kudzu, ocra, sago, sorghum, regular household potatoes, sweet potato, taro, yams, or one or more beans, such as favas, lentils or peas. Blends of any two or more starchy materials are also starchy materials. Mixtures of starchy, cellulosic and or lignocellulosic materials can also be used. For example, a biomass can be an entire plant, a part of a plant or different parts of a plant, e.g., a wheat plant, cotton plant, a corn plant, rice plant or a tree. The starchy materials can be treated by any of the methods described herein.

Microbial materials that can be used as feedstock can include, but are not limited to, any naturally occurring or genetically modified microorganism or organism that contains or is capable of providing a source of carbohydrates (e.g., cellulose), for example, protists, e.g., animal protists (e.g., protozoa such as *flagellates*, amoeboids, ciliates, and sporozoa) and plant protists (e.g., algae such alveolates, chlorarachniophytes, cryptomonads, euglenids, glaucophytes, haptophytes, red algae, stramenopiles, and viridaeplantae). Other examples include seaweed, plankton (e.g., macroplankton, mesoplankton, microplankton, nanoplankton, picoplankton, and femptoplankton), phytoplankton, bacteria (e.g., gram positive bacteria, gram negative bacteria, and extremophiles), yeast and/or mixtures of these. In some instances, microbial biomass can be obtained from natural sources, e.g., the ocean, lakes, bodies of water, e.g., salt water or fresh water, or on land. Alternatively or in addition, microbial biomass can be obtained from culture systems, e.g., large scale dry and wet culture and fermentation systems.

In other embodiments, the biomass materials, such as cellulosic, starchy and lignocellulosic feedstock materials, can be obtained from transgenic microorganisms and plants that have been modified with respect to a wild type variety. Such modifications may be, for example, through the iterative steps of selection and breeding to obtain desired traits in a plant. Furthermore, the plants can have had genetic material removed, modified, silenced and/or added with respect to the wild type variety. For example, genetically modified plants can be produced by recombinant DNA methods, where genetic modifications include introducing or modifying specific genes from parental varieties, or, for example, by using transgenic breeding wherein a specific gene or genes are introduced to a plant from a different species of plant and/or bacteria. Another way to create genetic variation is through mutation breeding wherein new alleles are artificially created from endogenous genes. The artificial genes can be created by a variety of ways including treating the plant or seeds with, for example, chemical mutagens (e.g., using alkylating agents, epoxides, alkaloids, peroxides, formaldehyde), irradiation (e.g., X-rays, gamma rays, neutrons, beta particles, alpha particles, protons, deuterons, UV radiation) and temperature shocking or other external stressing and subsequent selection techniques. Other methods of providing modified genes is through error prone PCR and DNA shuffling followed by insertion of the desired modified DNA into the desired plant or seed. Methods of introducing the desired genetic variation in the seed or plant include, for example, the use of a bacterial carrier, biolistics, calcium phosphate precipitation, electroporation, gene splicing, gene silencing, lipofection, microinjection and viral carriers. Additional genetically modified materials have been described in U.S. application Ser. No. 13/396,369 filed Feb. 14, 2012 the full disclosure of which is incorporated herein by reference.

Any of the methods described herein can be practiced with mixtures of any biomass materials described herein.

Other Materials

Other materials (e.g., natural or synthetic materials), for example, polymers, can be treated and/or made utilizing the methods, equipment and systems described herein. For example, polyethylene (e.g., linear low density ethylene and high density polyethylene), polystyrenes, sulfonated polystyrenes, poly (vinyl chloride), polyesters (e.g., nylons, DACRON™, KODEL™), polyalkylene esters, poly vinyl esters, polyamides (e.g., KEVLAR™) polyethylene terephthalate, cellulose acetate, acetal, poly acrylonitrile, polycarbonates (LEXAN™), acrylics [e.g., poly (methyl methacrylate), poly(methyl methacrylate), polyacrylonitrile], Poly urethanes, polypropylene, poly butadiene, polyisobutylene, polyacrylonitrile, polychloroprene (e.g. neoprene), poly(cis-1,4-isoprene) [e.g., natural rubber], poly (trans-1,4-isoprene) [e.g., gutta percha], phenol formaldehyde, melamine formaldehyde, epoxides, polyesters, poly amines, polycarboxylic acids, polylactic acids, polyvinyl alcohols, polyanhydrides, poly fluoro carbons (e.g., TEFLON™), silicons (e.g., silicone rubber), polysilanes, poly ethers (e.g., polyethylene oxide, polypropylene oxide), waxes, oils and mixtures of these. Also included are plastics, rubbers, elastomers, fibers, waxes, gels, oils, adhesives, thermoplastics, thermosets, biodegradable polymers, resins made with these polymers, other polymers, other materials and combinations thereof. The polymers can be made by any useful method including cationic polymerization, anionic polymerization, radical polymerization, metathesis polymerization, ring opening polymerization, graft polymerization, addition polymerization. In some cases the treatments disclosed herein can be used, for example, for radically initiated graft polymerization and cross linking. Composites of polymers, for example, with glass, metals, biomass (e.g., fibers, particles), ceramics can also be treated and/or made.

Other materials that can be treated by using the methods, systems and equipment disclosed herein are ceramic materials, minerals, metals, inorganic compounds. For example, silicon and germanium crystals, silicon nitrides, metal oxides, semiconductors, insulators, cements and or conductors.

In addition, manufactured multipart or shaped materials (e.g., molded, extruded, welded, riveted, layered or combined in any way) can be treated, for example, cables, pipes, boards, enclosures, integrated semiconductor chips, circuit boards, wires, tires, windows, laminated materials, gears, belts, machines, combinations of these. For example, treating a material by the methods described herein can modify the surfaces, for example, making them susceptible to further functionalization, combinations (e.g., welding) and/or treatment can cross link the materials.

Biomass Material Preparation—Mechanical Treatments

The biomass can be in a dry form, for example, with less than about 35% moisture content (e.g., less than about 20%, less than about 15%, less than about 10% less than about 5%, less than about 4%, less than about 3%, less than about 2% or even less than about 1%). The biomass can also be delivered in a wet state, for example as a wet solid, a slurry or a suspension with at least about 10 wt. % solids (e.g., at least about 20 wt. %, at least about 30 wt. %, at least about 40 wt. %, at least about 50 wt. %, at least about 60 wt. %, at least about 70 wt. %).

The processes disclosed herein can utilize low bulk density materials, for example cellulosic or lignocellulosic feedstocks that have been physically pretreated to have a bulk density of less than about 0.75 g/cm$^3$, e.g., less than about 0.7, 0.65, 0.60, 0.50, 0.35, 0.25, 0.20, 0.15, 0.10, 0.05 or less, e.g., less than about 0.025 g/cm$^3$. Bulk density is determined using ASTM D1895B. Briefly, the method involves filling a measuring cylinder of known volume with a sample and obtaining a weight of the sample. The bulk density is calculated by dividing the weight of the sample in grams by the known volume of the cylinder in cubic centimeters. If desired, low bulk density materials can be densified, for example, by methods described in U.S. Pat. No. 7,971,809 to Medoff, the full disclosure of which is hereby incorporated by reference.

In some cases, the pre-treatment processing includes screening of the biomass material. Screening can be through a mesh or perforated plate with a desired opening size, for example, less than about 6.35 mm (¼ inch, 0.25 inch), (e.g., less than about 3.18 mm (⅛ inch, 0.125 inch), less than about 1.59 mm (1/16 inch, 0.0625 inch), is less than about 0.79 mm (1/32 inch, 0.03125 inch), e.g., less than about 0.51 mm (1/50 inch, 0.02000 inch), less than about 0.40 mm (1/64 inch, 0.015625 inch), less than about 0.23 mm (0.009 inch), less than about 0.20 mm (1/128 inch, 0.0078125 inch), less than about 0.18 mm (0.007 inch), less than about 0.13 mm (0.005 inch), or even less than about 0.10 mm (1/256 inch, 0.00390625 inch)). In one configuration the desired biomass falls through the perforations or screen and thus biomass larger than the perforations or screen are not irradiated. These larger materials can be re-processed, for example, by comminuting, or they can simply be removed from processing. In another configuration material that is larger than the perforations is irradiated and the smaller material is removed by the screening process or recycled. In this kind of a configuration, the conveyor itself (for example, a part of the conveyor) can be perforated or made with a mesh. For example, in one particular embodiment the biomass material may be wet and the perforations or mesh allow water to drain away from the biomass before irradiation.

Screening of material can also be by a manual method, for example, by an operator or mechanoid (e.g., a robot equipped with a color, reflectivity or other sensor) that removes unwanted material. Screening can also be by magnetic screening wherein a magnet is disposed near the conveyed material and the magnetic material is removed magnetically.

Optional pre-treatment processing can include heating the material. For example, a portion of a conveyor conveying the biomass or other material can be sent through a heated zone. The heated zone can be created, for example, by IR radiation, microwaves, combustion (e.g., gas, coal, oil, biomass), resistive heating and/or inductive coils. The heat can be applied from at least one side or more than one side, can be continuous or periodic and can be for only a portion of the material or all the material. For example, a portion of the conveying trough can be heated by use of a heating jacket. Heating can be, for example, for the purpose of drying the material. In the case of drying the material, this can also be facilitated, with or without heating, by the movement of a gas (e.g., air, oxygen, nitrogen, He, $CO_2$, Argon) over and/or through the biomass as it is being conveyed.

Optionally, pre-treatment processing can include cooling the material. Cooling material is described in U.S. Pat. No. 7,900,857 to Medoff, the disclosure of which in incorporated herein by reference. For example, cooling can be by supplying a cooling fluid, for example, water (e.g., with glycerol), or nitrogen (e.g., liquid nitrogen) to the bottom of the conveying trough. Alternatively, a cooling gas, for example, chilled nitrogen can be blown over the biomass materials or under the conveying system.

Another optional pre-treatment processing method can include adding a material to the biomass or other feedstocks. The additional material can be added by, for example, by showering, sprinkling and or pouring the material onto the biomass as it is conveyed. Materials that can be added include, for example, metals, ceramics and/or ions as described in U.S. Pat. App. Pub. 2010/0105119 A1 (filed Oct. 26, 2009) and U.S. Pat. App. Pub. 2010/0159569 A1 (filed Dec. 16, 2009), the entire disclosures of which are incorporated herein by reference. Optional materials that can be added include acids and bases. Other materials that can be added are oxidants (e.g., peroxides, chlorates), polymers, polymerizable monomers (e.g., containing unsaturated bonds), water, catalysts, enzymes and/or organisms. Materials can be added, for example, in pure form, as a solution in a solvent (e.g., water or an organic solvent) and/or as a solution. In some cases the solvent is volatile and can be made to evaporate e.g., by heating and/or blowing gas as previously described. The added material may form a uniform coating on the biomass or be a homogeneous mixture of different components (e.g., biomass and additional material). The added material can modulate the subsequent irradiation step by increasing the efficiency of the irradiation, damping the irradiation or changing the effect of the irradiation (e.g., from electron beams to X-rays or heat). The method may have no impact on the irradiation but may be useful for further downstream processing. The added material may help in conveying the material, for example, by lowering dust levels.

Biomass can be delivered to a conveyor (e.g., vibratory conveyors that can be used in the vaults herein described) by a belt conveyor, a pneumatic conveyor, a screw conveyor, a hopper, a pipe, manually or by a combination of these. The biomass can, for example, be dropped, poured and/or placed onto the conveyor by any of these methods. In some embodiments the material is delivered to the conveyor using an enclosed material distribution system to help maintain a low oxygen atmosphere and/or control dust and fines. Lofted or air suspended biomass fines and dust are undesirable because these can form an explosion hazard or damage the window foils of an electron gun (if such a device is used for treating the material).

The material can be leveled to form a uniform thickness between about 0.0312 and 5 inches (e.g., between about 0.0625 and 2.000 inches, between about 0.125 and 1 inches, between about 0.125 and 0.5 inches, between about 0.3 and 0.9 inches, between about 0.2 and 0.5 inches between about 0.25 and 1.0 inches, between about 0.25 and 0.5 inches, 0.100+/−0.025 inches, 0.150+/−0.025 inches, 0.200+/−0.025 inches, 0.250+/−0.025 inches, 0.300+/−0.025 inches, 0.350+/−0.025 inches, 0.400+/−0.025 inches, 0.450+/−0.025 inches, 0.500+/−0.025 inches, 0.550+/−0.025 inches, 0.600+/−0.025 inches, 0.700+/−0.025 inches, 0.750+/−0.025 inches, 0.800+/−0.025 inches, 0.850+/−0.025 inches, 0.900+/−0.025 inches, 0.900+/−0.025 inches.

Generally, it is preferred to convey the material as quickly as possible through the electron beam to maximize throughput. For example, the material can be conveyed at rates of at least 1 ft/min, e.g., at least 2 ft/min, at least 3 ft/min, at least 4 ft/min, at least 5 ft/min, at least 10 ft/min, at least 15 ft/min, 20, 25, 30, 35, 40, 45, 50 ft/min. The rate of conveying is related to the beam current, for example, for a ¼ inch thick biomass and 100 mA, the conveyor can move at about 20 ft/min to provide a useful irradiation dosage, at 50 mA the conveyor can move at about 10 ft/min to provide approximately the same irradiation dosage.

After the biomass material has been conveyed through the radiation zone, optional post-treatment processing can be done. The optional post-treatment processing can, for example, be a process described with respect to the pre-irradiation processing. For example, the biomass can be screened, heated, cooled, and/or combined with additives. Uniquely to post-irradiation, quenching of the radicals can occur, for example, by the addition of fluids or gases (e.g., oxygen, nitrous oxide, ammonia and/or liquids), using pressure, heat, and/or the addition of radical scavengers. For example, the biomass can be conveyed out of the enclosed conveyor and exposed to a gas (e.g., oxygen) where it is quenched, forming carboxylated groups. In one embodiment, the biomass is exposed during irradiation to the reactive gas or fluid. Quenching of biomass that has been irradiated is described in U.S. Pat. No. 8,083,906 to Medoff, the entire disclosure of which is incorporate herein by reference.

If desired, one or more mechanical treatments can be used in addition to irradiation to further reduce the recalcitrance of the carbohydrate-containing material. These processes can be applied before, during and/or after irradiation.

In some cases, the mechanical treatment may include an initial preparation of the feedstock as received, e.g., size reduction of materials, such as by comminution, e.g., cutting, grinding, shearing, pulverizing or chopping. For example, in some cases, loose feedstock (e.g., recycled paper, starchy materials, or switchgrass) is prepared by shearing or shredding. Mechanical treatment may reduce the bulk density of the carbohydrate-containing material, increase the surface area of the carbohydrate-containing material and/or decrease one or more dimensions of the carbohydrate-containing material.

Alternatively, or in addition, the feedstock material can be treated with another treatment, for example, chemical treatments, such as an acid (HCl, $H_2SO_4$, $H_3PO_4$), a base (e.g., KOH and NaOH), a chemical oxidant (e.g., peroxides, chlorates, ozone), irradiation, steam explosion, pyrolysis, sonication, oxidation, chemical treatment. The treatments can be in any order and in any sequence and combinations. For example, the feedstock material can first be physically treated by one or more treatment methods, e.g., chemical treatment including and in combination with acid hydrolysis (e.g., utilizing HCl, $H_2SO_4$, $H_3PO_4$), radiation, sonication, oxidation, pyrolysis or steam explosion, and then mechanically treated. This sequence can be advantageous since materials treated by one or more of the other treatments, e.g., irradiation or pyrolysis, tend to be more brittle and, therefore, it may be easier to further change the structure of the material by mechanical treatment. As another example, a feedstock material can be conveyed through ionizing radiation using a conveyor as described herein and then mechanically treated. Chemical treatment can remove some or all of the lignin (for example, chemical pulping) and can partially or completely hydrolyze the material. The methods also can be used with pre-hydrolyzed material. The methods also can be used with material that has not been pre-hydrolyzed. The methods can be used with mixtures of hydrolyzed and non-hydrolyzed materials, for example, with about 50% or more non-hydrolyzed material, with about 60% or more non-hydrolyzed material, with about 70% or more non-hydrolyzed material, with about 80% or more non-hydrolyzed material or even with 90% or more non-hydrolyzed material.

In addition to size reduction, which can be performed initially and/or later in processing, mechanical treatment can also be advantageous for "opening up," "stressing," breaking or shattering the carbohydrate-containing materials, making the cellulose of the materials more susceptible to chain scission and/or disruption of crystalline structure during the physical treatment.

Methods of mechanically treating the carbohydrate-containing material include, for example, milling or grinding. Milling may be performed using, for example, a hammer mill, ball mill, colloid mill, conical or cone mill, disk mill, edge mill, Wiley mill, grist mill or other mill. Grinding may be performed using, for example, a cutting/impact type grinder. Some exemplary grinders include stone grinders, pin grinders, coffee grinders, and burr grinders. Grinding or milling may be provided, for example, by a reciprocating pin or other element, as is the case in a pin mill. Other mechanical treatment methods include mechanical ripping or tearing, other methods that apply pressure to the fibers, and air attrition milling. Suitable mechanical treatments further include any other technique that continues the disruption of the internal structure of the material that was initiated by the previous processing steps.

Mechanical feed preparation systems can be configured to produce streams with specific characteristics such as, for example, specific maximum sizes, specific length-to-width, or specific surface areas ratios. Physical preparation can increase the rate of reactions, improve the movement of material on a conveyor, improve the irradiation profile of the material, improve the radiation uniformity of the material, or reduce the processing time required by opening up the materials and making them more accessible to processes and/or reagents, such as reagents in a solution.

The bulk density of feedstocks can be controlled (e.g., increased). In some situations, it can be desirable to prepare a low bulk density material, e.g., by densifying the material (e.g., densification can make it easier and less costly to transport to another site) and then reverting the material to a lower bulk density state (e.g., after transport). The material can be densified, for example, from less than about 0.2 g/cc to more than about 0.9 g/cc (e.g., less than about 0.3 to more than about 0.5 g/cc, less than about 0.3 to more than about 0.9 g/cc, less than about 0.5 to more than about 0.9 g/cc, less than about 0.3 to more than about 0.8 g/cc, less than about 0.2 to more than about 0.5 g/cc). For example, the material can be densified by the methods and equipment disclosed in U.S. Pat. No. 7,932,065 to Medoff and International Publication No. WO 2008/073186 (which was filed Oct. 26, 2007, was published in English, and which designated the United States), the full disclosures of which are incorporated herein by reference. Densified materials can be processed by any of the methods described herein, or any material processed by any of the methods described herein can be subsequently densified.

In some embodiments, the material to be processed is in the form of a fibrous material that includes fibers provided by shearing a fiber source. For example, the shearing can be performed with a rotary knife cutter.

For example, a fiber source, e.g., that is recalcitrant or that has had its recalcitrance level reduced, can be sheared, e.g., in a rotary knife cutter, to provide a first fibrous material. The first fibrous material is passed through a first screen, e.g., having an average opening size of 1.59 mm or less (1/16 inch, 0.0625 inch), provide a second fibrous material. If desired, the fiber source can be cut prior to the shearing, e.g., with a shredder. For example, when a paper is used as the fiber source, the paper can be first cut into strips that are, e.g., 1/4-to 1/2-inch wide, using a shredder, e.g., a counter-rotating screw shredder, such as those manufactured by Munson (Utica, N.Y.). As an alternative to shredding, the paper can be reduced in size by cutting to a desired size using a guillotine cutter. For example, the guillotine cutter can be used to cut the paper into sheets that are, e.g., 10 inches wide by 12 inches long.

In some embodiments, the shearing of the fiber source and the passing of the resulting first fibrous material through a first screen are performed concurrently. The shearing and the passing can also be performed in a batch-type process.

For example, a rotary knife cutter can be used to concurrently shear the fiber source and screen the first fibrous material. A rotary knife cutter includes a hopper that can be loaded with a shredded fiber source prepared by shredding a fiber source.

In some implementations, the feedstock is physically treated prior to saccharification and/or fermentation. Physical treatment processes can include one or more of any of those described herein, such as mechanical treatment, chemical treatment, irradiation, sonication, oxidation, pyrolysis or steam explosion. Treatment methods can be used in combinations of two, three, four, or even all of these technologies (in any order). When more than one treatment method is used, the methods can be applied at the same time or at different times. Other processes that change a molecular structure of a biomass feedstock may also be used, alone or in combination with the processes disclosed herein.

Mechanical treatments that may be used, and the characteristics of the mechanically treated carbohydrate-containing materials, are described in further detail in U.S. Pat. App. Pub. 2012/0100577 A1, filed Oct. 18, 2011, the full disclosure of which is hereby incorporated herein by reference.

Sonication, Pyrolysis, Oxidation, Steam Explosion

If desired, one or more sonication, pyrolysis, oxidative, or steam explosion processes can be used, instead of or in addition to, irradiation to reduce or further reduce the recalcitrance of the carbohydrate-containing material. For example, these processes can be applied before, during and/or after irradiation. These processes are described in detail in U.S. Pat. No. 7,932,065 to Medoff, the full disclosure of which is incorporated herein by reference.

Intermediates and Products

Using the processes described herein, the biomass material can be converted to one or more products, such as energy, fuels, foods and materials. For example, intermediates and products such as organic acids, salts of organic acids, anhydrides, esters of organic acids and fuels, e.g., fuels for internal combustion engines or feedstocks for fuel cells. Systems and processes are described herein that can use as feedstock cellulosic and/or lignocellulosic materials that are readily available, but often can be difficult to process, e.g., municipal waste streams and waste paper streams, such as streams that include newspaper, Kraft paper, corrugated paper or mixtures of these.

Specific examples of products include, but are not limited to, hydrogen, sugars (e.g., glucose, xylose, arabinose, mannose, galactose, fructose, disaccharides, oligosaccharides and polysaccharides), alcohols (e.g., monohydric alcohols or dihydric alcohols, such as ethanol, n-propanol, isobutanol, sec-butanol, tert-butanol or n-butanol), hydrated or hydrous alcohols (e.g., containing greater than 10%, 20%, 30% or even greater than 40% water), biodiesel, organic acids, hydrocarbons (e.g., methane, ethane, propane, isobutene, pentane, n-hexane, biodiesel, bio-gasoline and mixtures thereof), co-products (e.g., proteins, such as cellulolytic proteins (enzymes) or single cell proteins), and mixtures of any of these in any combination or relative concentration, and optionally, in combination with any additives (e.g., fuel additives). Other examples include carboxylic acids, salts of a carboxylic acid, a mixture of carboxylic acids and salts of carboxylic acids and esters of carboxylic acids (e.g., methyl, ethyl and n-propyl esters), ketones (e.g., acetone), aldehydes (e.g., acetaldehyde), alpha and beta unsaturated acids (e.g., acrylic acid) and olefins (e.g., ethylene). Other alcohols and alcohol derivatives include propanol, propylene glycol, 1,4-butanediol, 1,3-propanediol, sugar alcohols (e.g., erythritol, glycol, glycerol, sorbitol threitol, arabitol, ribitol, mannitol, dulcitol, fucitol, iditol, isomalt, maltitol, lactitol, xylitol and other polyols), and methyl or ethyl esters of any of these alcohols. Other products include methyl acrylate, methylmethacrylate, D-lactic acid, L-lactic acid, pyruvic acid, poly lactic acid, citric acid, formic acid, acetic acid, propionic acid, butyric acid, succinic acid, valeric acid, caproic acid, 3-hydroxypropionic acid, palmitic acid, stearic acid, oxalic acid, malonic acid, glutaric acid, oleic acid, linoleic acid, glycolic acid, gamma-hydroxybutyric acid, and mixtures thereof, salts of any of these acids, mixtures of any of the acids and their respective salts.

Any combination of the above products with each other, and/or of the above products with other products, which other products may be made by the processes described herein or otherwise, may be packaged together and sold as products. The products may be combined, e.g., mixed, blended or co-dissolved, or may simply be packaged or sold together.

Any of the products or combinations of products described herein may be sanitized or sterilized prior to selling the products, e.g., after purification or isolation or even after packaging, to neutralize one or more potentially undesirable contaminants that could be present in the product(s). Such sanitation can be done with electron bombardment, for example, be at a dosage of less than about 20 Mrad, e.g., from about 0.1 to 15 Mrad, from about 0.5 to 7 Mrad, or from about 1 to 3 Mrad.

The processes described herein can produce various by-product streams useful for generating steam and electricity to be used in other parts of the plant (co-generation) or sold on the open market. For example, steam generated from burning by-product streams can be used in a distillation process. As another example, electricity generated from burning by-product streams can be used to power electron beam generators used in pretreatment.

The by-products used to generate steam and electricity are derived from a number of sources throughout the process. For example, anaerobic digestion of wastewater can produce a biogas high in methane and a small amount of waste biomass (sludge). As another example, post-saccharification and/or post-distillate solids (e.g., unconverted lignin, cellulose, and hemicellulose remaining from the pretreatment and primary processes) can be used, e.g., burned, as a fuel.

Other intermediates and products, including food and pharmaceutical products, are described in U.S. Pat. App. Pub. 2010/0124583 A1, published May 20, 2010, to Medoff, the full disclosure of which is hereby incorporated by reference herein.

Lignin Derived Products

The spent biomass (e.g., spent lignocellulosic material) from lignocellulosic processing by the methods described are expected to have a high lignin content and in addition to being useful for producing energy through combustion in a Co-Generation plant, may have uses as other valuable products. For example, the lignin can be used as captured as a plastic, or it can be synthetically upgraded to other plastics. In some instances, it can also be converted to lignosulfonates, which can be utilized as binders, dispersants, emulsifiers or sequestrants.

When used as a binder, the lignin or a lignosulfonate can, e.g., be utilized in coal briquettes, in ceramics, for binding carbon black, for binding fertilizers and herbicides, as a dust suppressant, in the making of plywood and particle board, for binding animal feeds, as a binder for fiberglass, as a binder in linoleum paste and as a soil stabilizer.

When used as a dispersant, the lignin or lignosulfonates can be used, for example in, concrete mixes, clay and ceramics, dyes and pigments, leather tanning and in gypsum board.

When used as an emulsifier, the lignin or lignosulfonates can be used, e.g., in asphalt, pigments and dyes, pesticides and wax emulsions.

As a sequestrant, the lignin or lignosulfonates can be used, e.g., in micro-nutrient systems, cleaning compounds and water treatment systems, e.g., for boiler and cooling systems.

For energy production lignin generally has a higher energy content than holocellulose (cellulose and hemicellulose) since it contains more carbon than homocellulose. For example, dry lignin can have an energy content of between about 11,000 and 12,500 BTU per pound, compared to 7,000 an 8,000 BTU per pound of holocellulose. As such, lignin can be densified and converted into briquettes and pellets for burning. For example, the lignin can be converted into pellets by any method described herein. For a slower burning pellet or briquette, the lignin can be crosslinked, such as applying a radiation dose of between about 0.5 Mrad and 5 Mrad. Crosslinking can make a slower burning form factor. The form factor, such as a pellet or briquette, can be converted to a "synthetic coal" or charcoal by pyrolyzing in the absence of air, e.g., at between 400 and 950° C. Prior to pyrolyzing, it can be desirable to crosslink the lignin to maintain structural integrity.

Saccharification

In order to convert the feedstock to a form that can be readily processed, the glucan- or xylan-containing cellulose in the feedstock can be hydrolyzed to low molecular weight carbohydrates, such as sugars, by a saccharifying agent, e.g., an enzyme or acid, a process referred to as saccharification. The low molecular weight carbohydrates can then be used, for example, in an existing manufacturing plant, such as a single cell protein plant, an enzyme manufacturing plant, or a fuel plant, e.g., an ethanol manufacturing facility.

The feedstock can be hydrolyzed using an enzyme, e.g., by combining the materials and the enzyme in a solvent, e.g., in an aqueous solution.

Alternatively, the enzymes can be supplied by organisms that break down biomass, such as the cellulose and/or the lignin portions of the biomass, contain or manufacture various cellulolytic enzymes (cellulases), ligninases or various small molecule biomass-degrading metabolites. These enzymes may be a complex of enzymes that act synergistically to degrade crystalline cellulose or the lignin portions of biomass. Examples of cellulolytic enzymes include: endoglucanases, cellobiohydrolases, and cellobiases (beta-glucosidases).

During saccharification, a cellulosic substrate can be initially hydrolyzed by endoglucanases at random locations producing oligomeric intermediates. These intermediates are then substrates for exo-splitting glucanases such as cellobiohydrolase to produce cellobiose from the ends of the cellulose polymer. Cellobiose is a water-soluble 1,4-linked dimer of glucose. Finally, cellobiase cleaves cellobiose to yield glucose. The efficiency (e.g., time to hydrolyze and/or completeness of hydrolysis) of this process depends on the recalcitrance of the cellulosic material.

Therefore, the treated biomass materials can be saccharified, generally by combining the material and a cellulase enzyme in a fluid medium, e.g., an aqueous solution. In some cases, the material is boiled, steeped, or cooked in hot water prior to saccharification, as described in U.S. Pat. App. Pub. 2012/0100577 A1 by Medoff and Masterman, published on Apr. 26, 2012, the entire contents of which are incorporated herein.

The saccharification process can be partially or completely performed in a tank (e.g., a tank having a volume of at least 4000, 40,000, or 500,000 L) in a manufacturing plant, and/or can be partially or completely performed in transit, e.g., in a rail car, tanker truck, or in a supertanker or the hold of a ship. The time required for complete saccharification will depend on the process conditions and the carbohydrate-containing material and enzyme used. If saccharification is performed in a manufacturing plant under controlled conditions, the cellulose may be substantially entirely converted to sugar, e.g., glucose in about 12-96 hours. If saccharification is performed partially or completely in transit, saccharification may take longer.

It is generally preferred that the tank contents be mixed during saccharification, e.g., using jet mixing as described in International App. No. PCT/US2010/035331, filed May 18, 2010, which was published in English as WO 2010/135380 and designated the United States, the full disclosure of which is incorporated by reference herein.

The addition of surfactants can enhance the rate of saccharification. Examples of surfactants include non-ionic surfactants, such as a Tween® 20 or Tween® 80 polyethylene glycol surfactants, ionic surfactants, or amphoteric surfactants.

It is generally preferred that the concentration of the sugar solution resulting from saccharification be relatively high, e.g., greater than 40%, or greater than 50, 60, 70, 80, 90 or even greater than 95% by weight. Water may be removed, e.g., by evaporation, to increase the concentration of the sugar solution. This reduces the volume to be shipped, and also inhibits microbial growth in the solution.

Alternatively, sugar solutions of lower concentrations may be used, in which case it may be desirable to add an antimicrobial additive, e.g., a broad spectrum antibiotic, in a low concentration, e.g., 50 to 150 ppm. Other suitable antibiotics include amphotericin B, ampicillin, chloramphenicol, ciprofloxacin, gentamicin, hygromycin B, kanamycin, neomycin, penicillin, puromycin, streptomycin. Antibiotics will inhibit growth of microorganisms during transport and storage, and can be used at appropriate concentrations, e.g., between 15 and 1000 ppm by weight, e.g., between 25 and 500 ppm, or between 50 and 150 ppm. If desired, an antibiotic can be included even if the sugar concentration is relatively high. Alternatively, other additives with anti-microbial preservative properties may be used. Preferably the antimicrobial additive(s) are food-grade.

A relatively high concentration solution can be obtained by limiting the amount of water added to the carbohydrate-containing material with the enzyme. The concentration can be controlled, e.g., by controlling how much saccharification takes place. For example, concentration can be increased by adding more carbohydrate-containing material to the solution. In order to keep the sugar that is being produced in solution, a surfactant can be added, e.g., one of those discussed above. Solubility can also be increased by increasing the temperature of the solution. For example, the solution can be maintained at a temperature of 40-50° C., 60-80° C., or even higher.

Saccharifying Agents

Suitable cellulolytic enzymes include cellulases from species in the genera *Bacillus, Coprinus, Myceliophthora, Cephalosporium, Scytalidium, Penicillium, Aspergillus, Pseudomonas, Humicola, Fusarium, Thielavia, Acremonium, Chrysosporium* and *Trichoderma*, especially those produced by a strain selected from the species *Aspergillus* (see, e.g., EP Pub. No. 0 458 162), *Humicola insolens* (reclassified as *Scytalidium thermophilum*, see, e.g., U.S. Pat. No. 4,435,307), *Coprinus cinereus, Fusarium oxysporum, Myceliophthora thermophila, Meripilus giganteus, Thielavia terrestris, Acremonium* sp. (including, but not limited to, *A. persicinum, A. acremonium, A. brachypenium, A. dichromosporum, A. obclavatum, A. pinkertoniae, A. roseogriseum, A. incoloratum,* and *A. furatum*). Preferred strains include *Humicola insolens* DSM 1800, *Fusarium oxysporum* DSM 2672, *Myceliophthora thermophila* CBS 117.65, *Cephalosporium* sp. RYM-202, *Acremonium* sp. CBS 478.94, *Acremonium* sp. CBS 265.95, *Acremonium persicinum* CBS 169.65, *Acremonium acremonium* AHU 9519, *Cephalosporium* sp. CBS 535.71, *Acremonium brachypenium* CBS 866.73, *Acremonium dichromosporum* CBS 683.73, *Acremonium obclavatum* CBS 311.74, *Acremonium pinkertoniae* CBS 157.70, *Acremonium roseogriseum* CBS 134.56, *Acremonium incoloratum* CBS 146.62, and *Acremonium furatum* CBS 299.70H. Cellulolytic enzymes may also be obtained from *Chrysosporium*, preferably a strain of *Chrysosporium lucknowense*. Additional strains that can be used include, but are not limited to, *Trichoderma* (particularly *T. viride, T. reesei,* and *T. koningii*), alkalophilic *Bacillus* (see, for example, U.S. Pat. No. 3,844,890 and EP Pub. No. 0 458 162), and *Streptomyces* (see, e.g., EP Pub. No. 0 458 162).

In addition to or in combination to enzymes, acids, bases and other chemicals (e.g., oxidants) can be utilized to saccharify lignocellulosic and cellulosic materials. These can be used in any combination or sequence (e.g., before, after and/or during addition of an enzyme). For example, strong mineral acids can be utilized (e.g. HCl, $H_2SO_4$, $H_3PO_4$) and strong bases (e.g., NaOH, KOH).

Sugars

In the processes described herein, for example, after saccharification, sugars (e.g., glucose and xylose) can be isolated. For example, sugars can be isolated by precipitation, crystallization, chromatography (e.g., simulated moving bed chromatography, high pressure chromatography), centrifugation, extraction, any other isolation method known in the art, and combinations thereof.

Hydrogenation and Other Chemical Transformations

The processes described herein can include hydrogenation. For example, glucose and xylose can be hydrogenated to sorbitol and xylitol, respectively. Hydrogenation can be accomplished by use of a catalyst (e.g., Pt/gamma-$Al_2O_3$, Ru/C, Raney Nickel, or other catalysts known in the art) in combination with $H_2$ under high pressure (e.g., 10 to 12000 psi). Other types of chemical transformation of the products from the processes described herein can be used, for example, production of organic sugar derived products (e.g., furfural and furfural-derived products). Chemical transformations of sugar derived products are described in U.S. Ser. No. 13/934,704 filed Jul. 3, 2013, the entire disclosure of which is incorporated herein by reference.

Fermentation

Yeast and *Zymomonas* bacteria, for example, can be used for fermentation or conversion of sugar(s) to alcohol(s). Other microorganisms are discussed below. The optimum pH for fermentations is about pH 4 to 7. For example, the optimum pH for yeast is from about pH 4 to 5, while the optimum pH for *Zymomonas* is from about pH 5 to 6.

Typical fermentation times are about 24 to 168 hours (e.g., 24 to 96 hrs) with temperatures in the range of 20° C. to 40° C. (e.g., 26° C. to 40° C.); however thermophilic microorganisms prefer higher temperatures.

In some embodiments, e.g., when anaerobic organisms are used, at least a portion of the fermentation is conducted in the absence of oxygen, e.g., under a blanket of an inert gas such as $N_2$, Ar, He, $CO_2$ or mixtures thereof. Additionally, the mixture may have a constant purge of an inert gas flowing through the tank during part of or all of the fermentation. In some cases, anaerobic conditions can be achieved or maintained by carbon dioxide production during the fermentation and no additional inert gas is needed.

In some embodiments, all or a portion of the fermentation process can be interrupted before the low molecular weight sugar is completely converted to a product (e.g., ethanol). The intermediate fermentation products include sugar and carbohydrates in high concentrations. The sugars and carbohydrates can be isolated via any means known in the art. These intermediate fermentation products can be used in preparation of food for human or animal consumption. Additionally or alternatively, the intermediate fermentation products can be ground to a fine particle size in a stainless-steel laboratory mill to produce a flour-like substance. Jet mixing may be used during fermentation, and in some cases saccharification and fermentation are performed in the same tank.

Nutrients for the microorganisms may be added during saccharification and/or fermentation, for example, the food-based nutrient packages described in U.S. Pat. App. Pub. 2012/0052536, filed Jul. 15, 2011, the complete disclosure of which is incorporated herein by reference.

"Fermentation" includes the methods and products that are disclosed in application Nos. PCT/US2012/71093 published Jun. 27, 2013, PCT/US2012/71907 published Jun. 27, 2012, and PCT/US2012/71083 published Jun. 27, 2012 the contents of which are incorporated by reference herein in their entirety.

Mobile fermenters can be utilized, as described in International App. No. PCT/US2007/074028 (which was filed Jul. 20, 2007, was published in English as WO 2008/011598 and designated the United States) and has a US issued U.S. Pat. No. 8,318,453, the contents of which are incorporated herein in its entirety. Similarly, the saccharification equipment can be mobile. Further, saccharification and/or fermentation may be performed in part or entirely during transit.

Fermentation Agents

The microorganism(s) used in fermentation can be naturally-occurring microorganisms and/or engineered microorganisms. For example, the microorganism can be a bacterium (including, but not limited to, e.g., a cellulolytic bacterium), a fungus, (including, but not limited to, e.g., a yeast), a plant, a protist, e.g., a protozoa or a fungus-like protest (including, but not limited to, e.g., a slime mold), or an alga. When the organisms are compatible, mixtures of organisms can be utilized.

Suitable fermenting microorganisms have the ability to convert carbohydrates, such as glucose, fructose, xylose, arabinose, mannose, galactose, oligosaccharides or polysaccharides into fermentation products. Fermenting microorganisms include strains of the genus *Saccharomyces* spp. (including, but not limited to, *S. cerevisiae* (baker's yeast), *S. distaticus*, *S. uvarum*), the genus *Kluyveromyces*, (including, but not limited to, *K. marxianus*, *K. fragilis*), the genus *Candida* (including, but not limited to, *C. pseudotropicalis*, and *C. brassicae*), *Pichia stipitis* (a relative of *Candida shehatae*), the genus *Clavispora* (including, but not limited to, *C. lusitaniae* and *C. opuntiae*), the genus *Pachysolen* (including, but not limited to, *P. tannophilus*), the genus *Bretannomyces* (including, but not limited to, e.g., *B. clausenii* (Philippidis, G. P., 1996, Cellulose Bioconversion Technology, in Handbook on Bioethanol: Production and Utilization, Wyman, C. E., ed., Taylor & Francis, Washington, D.C., 179-212)). Other suitable microorganisms include, for example, *Zymomonas mobilis*, *Clostridium* spp. (including, but not limited to, *C. thermocellum* (Philippidis, 1996, supra), *C. saccharobutylacetonicum*, *C. tyrobutyricum* *C. saccharobutylicum*, *C. Puniceum*, *C. beijernckii*, and *C. acetobutylicum*), *Moniliella* spp. (including but not limited to *M. pollinis*, *M. tomentosa*, *M. madida*, *M. nigrescens*, *M. oedocephali*, *M. megachiliensis*), *Yarrowia lipolytica*, *Aureobasidium* sp., *Trichosporonoides* sp., *Trigonopsis variabilis*, *Trichosporon* sp., *Moniliellaacetoabutans* sp., *Typhula variabilis*, *Candida magnoliae*, *Ustilaginomycetes* sp., *Pseudozyma tsukubaensis*, yeast species of genera *Zygosaccharomyces*, *Debaryomyces*, *Hansenula* and *Pichia*, and fungi of the dematioid genus *Torula* (e.g., *T. corallina*).

Additional microorganisms include the *Lactobacillus* group. Examples include *Lactobacillus casei*, *Lactobacillus rhamnosus*, *Lactobacillus delbrueckii*, *Lactobacillus plantarum*, *Lactobacillus coryniformis*, e.g., *Lactobacillus coryniformis* subspecies torquens, *Lactobacillus pentosus*, *Lactobacillus brevis*. Other microorganisms include *Pediococus penosaceus*, *Rhizopus oryzae*.

Several organisms, such as bacteria, yeasts and fungi, can be utilized to ferment biomass derived products such as sugars and alcohols to succinic acid and similar products. For example, organisms can be selected from; *Actinobacillus succinogenes*, *Anaerobiospirillum succiniciproducens*, *Mannheimia succiniciproducens*, *Ruminococcus flaverfaciens*, *Ruminococcus albus*, *Fibrobacter succinogenes*, *Bacteroides fragilis*, *Bacteroides ruminicola*, *Bacteroides amylophilus*, *Bacteroides succinogenes*, *Mannheimia succiniciproducens*, *Corynebacterium glutamicum*, *Aspergillus niger*, *Aspergillus fumigatus*, *Byssochlamys nivea*, *Lentinus degener*, *Paecilomyces varioti*, *Penicillium viniferum*, *Saccharomyces cerevisiae*, *Enterococcus faecali*, *Prevotella ruminicolas*, *Debaryomyces hansenii*, *Candida catenulata* VKM Y-5, *C. mycoderma* VKM Y-240, *C. rugosa* VKM Y-67, *C. paludigena* VKM Y-2443, *C. utilis* VKM Y-74, *C. utilis* 766, *C. zeylanoides* VKM Y-6, *C. zeylanoides* VKM Y-14, *C. zeylanoides* VKM Y-2324, *C. zeylanoides* VKM Y-1543, *C. zeylanoides* VKM Y-2595, *C. valida* VKM Y-934, *Kluyveromyces wickerhamii* VKM Y-589, *Pichia anomala* VKM Y-118, *P. besseyi* VKM Y-2084, *P. media* VKM Y-1381, *P. guilliermondii* H-P-4, *P. guilliermondii* 916, *P. inositovora* VKM Y-2494, *Saccharomyces cerevisiae* VKM Y-381, *Torulopsis candida* 127, *T. candida* 420, *Yarrowia lipolytica* 12a, *Y. lipolytica* VKM Y-47, *Y. lipolytica* 69, *Y. lipolytica* VKM Y-57, *Y. lipolytica* 212, *Y. lipolytica* 374/4, *Y. lipolytica* 585, *Y. lipolytica* 695, *Y. lipolytica* 704, and mixtures of these organisms.

Many such microbial strains are publicly available, either commercially or through depositories such as the ATCC (American Type Culture Collection, Manassas, Va., USA), the NRRL (Agricultural Research Service Culture Collection, Peoria, Ill., USA), or the DSMZ (Deutsche Sammlung von Mikroorganismen und Zellkulturen GmbH, Braunschweig, Germany), to name a few.

Commercially available yeasts include, for example, RED STAR®/Lesaffre Ethanol Red (available from Red Star/Lesaffre, USA), FALI® (available from Fleischmann's Yeast, a division of Burns Philip Food Inc., USA), SUPER-START® (available from Alltech, now Lalemand), GERT STRAND® (available from Gert Strand AB, Sweden) and FERMOL® (available from DSM Specialties).

Distillation

After fermentation, the resulting fluids can be distilled using, for example, a "beer column" to separate ethanol and other alcohols from the majority of water and residual solids. The vapor exiting the beer column can be, e.g., 35% by weight ethanol and can be fed to a rectification column. A mixture of nearly azeotropic (92.5%) ethanol and water from the rectification column can be purified to pure (99.5%) ethanol using vapor-phase molecular sieves. The beer column bottoms can be sent to the first effect of a three-effect evaporator. The rectification column reflux condenser can provide heat for this first effect. After the first effect, solids can be separated using a centrifuge and dried in a rotary dryer. A portion (25%) of the centrifuge effluent can be recycled to fermentation and the rest sent to the second and third evaporator effects. Most of the evaporator condensate can be returned to the process as fairly clean condensate with a small portion split off to waste water treatment to prevent build-up of low-boiling compounds.

Hydrocarbon-Containing Materials

In other embodiments utilizing the methods and systems described herein, hydrocarbon-containing materials can be processed. Any process described herein can be used to treat any hydrocarbon-containing material herein described. "Hydrocarbon-containing materials," as used herein, is meant to include oil sands, oil shale, tar sands, coal dust, coal slurry, bitumen, various types of coal, and other naturally-occurring and synthetic materials that include both hydrocarbon components and solid matter. The solid matter can include wood, rock, sand, clay, stone, silt, drilling slurry, or other solid organic and/or inorganic matter. The term can also include waste products such as drilling waste and by-products, refining waste and by-products, or other waste products containing hydrocarbon components, such as asphalt shingling and covering, asphalt pavement, etc.

In yet other embodiments utilizing the methods and systems described herein, wood and wood containing produces can be processed. For example lumber products can be processed, e.g. boards, sheets, laminates, beams, particle boards, composites, rough cut wood, soft wood and hard wood. In addition cut trees, bushes, wood chips, saw dust, roots, bark, stumps, decomposed wood and other wood containing biomass material can be processed.

Conveying Systems

Various conveying systems can be used to convey the biomass material, for example, as discussed, to a vault, and under an electron beam in a vault. Exemplary conveyors are belt conveyors, pneumatic conveyors, screw conveyors, carts, trains, trains or carts on rails, elevators, front loaders, backhoes, cranes, various scrapers and shovels, trucks, and throwing devices can be used. For example, vibratory conveyors can be used in various processes described herein. Vibratory conveyors are described in PCT/US2013/64289 filed Oct. 10, 2013 the full disclosure of which is incorporated by reference herein.

Vibratory conveyors are particularly useful for spreading the material and producing a uniform layer on the conveyor trough surface. For example the initial feedstock can form a pile of material that can be at least four feet high (e.g., at least about 3 feet, at least about 2 feet, at least about 1 foot, at least about 6 inches, at least about 5 inches, at least about, 4 inches, at least about 3 inches, at least about 2 inches, at least about 1 inch, at least about ½ inch) and spans less than the width of the conveyor (e.g., less than about 10%, less than about 20%, less than about 30%, less than about 40%, less than about 50%, less than about 60%, less than about 70%, less than about 80%, less than about 90%, less than about 95%, less than about 99%). The vibratory conveyor can spread the material to span the entire width of the conveyor trough and have a uniform thickness, preferably as discussed above. In some cases, an additional spreading method can be useful. For example, a spreader such as a broadcast spreader, a drop spreader (e.g., a CHRISTY SPREADER™) or combinations thereof can be used to drop (e.g., place, pour, spill and/or sprinkle) the feedstock over a wide area. Optionally, the spreader can deliver the biomass as a wide shower or curtain onto the vibratory conveyor. Additionally, a second conveyor, upstream from the first conveyor (e.g., the first conveyor is used in the irradiation of the feedstock), can drop biomass onto the first conveyor, where the second conveyor can have a width transverse to the direction of conveying smaller than the first conveyor. In particular, when the second conveyor is a vibratory conveyor, the feedstock is spread by the action of the second and first conveyor. In some optional embodiments, the second conveyor ends in a bias cross cut discharge (e.g., a bias cut with a ratio of 4:1) so that the material can be dropped as a wide curtain (e.g., wider than the width of the second conveyor) onto the first conveyor. The initial drop area of the biomass by the spreader (e.g., broadcast spreader, drop spreader, conveyor, or cross cut vibratory conveyor) can span the entire width of the first vibratory conveyor, or it can span part of this width. Once dropped onto the conveyor, the material is spread even more uniformly by the vibrations of the conveyor so that, preferably, the entire width of the conveyor is covered with a uniform layer of biomass. In some embodiments combinations of spreaders can be used. Some methods of spreading a feed stock are described in U.S. Pat. No. 7,153,533, filed Jul. 23, 2002 and published Dec. 26, 2006, the entire disclosure of which is incorporated herein by reference.

Generally, it is preferred to convey the material as quickly as possible through an electron beam to maximize throughput. For example, the material can be conveyed at rates of at least 1 ft/min, e.g., at least 2 ft/min, at least 3 ft/min, at least 4 ft/min, at least 5 ft/min, at least 10 ft/min, at least 15 ft/min, at least 20 ft/min, at least 25 ft/min, at least 30 ft/min, at least 40 ft/min, at least 50 ft/min, at least 60 ft/min, at least 70 ft/min, at least 80 ft/min, at least 90 ft/min. The rate of conveying is related to the beam current and targeted irradiation dose, for example, for a ¼ inch thick biomass spread over a 5.5 foot wide conveyor and 100 mA, the conveyor can move at about 20 ft/min to provide a useful irradiation dosage (e.g. about 10 Mrad for a single pass), at 50 mA the conveyor can move at about 10 ft/min to provide approximately the same irradiation dosage.

The rate at which material can be conveyed depends on the shape and mass of the material being conveyed and the desired treatment. Flowing materials e.g., particulate materials, are particularly amenable to conveying with vibratory conveyors. Conveying speeds can, for example be, at least 100 lb/hr (e.g., at least 500 lb/hr, at least 1000 lb/hr, at least 2000 lb/hr, at least 3000 lb/hr, at least 4000 lb/hr, at least 5000 lb/hr, at least 10,000 lb/hr, at least 15,000 lb/hr, or even at least 25,000 lb/hr). Some typical conveying speeds can be between about 1000 and 10,000 lb/hr, (e.g., between about 1000 lb/hr and 8000 lb/hr, between about 2000 and 7000 lb/hr, between about 2000 and 6000 lb/hr, between about 2000 and 5000 lb/hr, between about 2000 and 4500 lb/hr, between about 1500 and 5000 lb/hr, between about 3000 and 7000 lb/hr, between about 3000 and 6000 lb/hr, between about 4000 and 6000 lb/hr and between about 4000 and 5000 lb/hr). Typical conveying speeds depend on the density of the material. For example, for a biomass with a density of about 35 lb/ft3, and a conveying speed of about 5000 lb/hr, the material is conveyed at a rate of about 143 ft3/hr, if the material is ¼" thick and is in a trough 5.5 ft wide, the material is conveyed at a rate of about 1250 ft/hr (about 21 ft/min). Rates of conveying the material can therefore vary greatly. Preferably, for example, a ¼" thick layer of biomass, is conveyed at speeds of between about 5 and 100 ft/min (e.g. between about 5 and 100 ft/min, between about 6 and 100 ft/min, between about 7 and 100 ft/min, between about 8 and 100 ft/min, between about 9 and 100 ft/min, between about 10 and 100 ft/min, between about 11 and 100 ft/min, between about 12 and 100 ft/min, between about 13 and 100 ft/min, between about 14 and 100 ft/min, between about 15 and 100 ft/min, between about 20 and 100 ft/min, between about 30 and 100 ft/min, between about 40 and 100 ft/min, between about 2 and 60 ft/min, between about 3 and 60 ft/min, between about 5 and 60 ft/min, between about 6 and 60 ft/min, between about 7 and 60 ft/min, between about 8 and 60 ft/min, between about 9 and 60 ft/min, between about 10 and 60 ft/min, between about 15 and 60 ft/min, between about 20 and 60 ft/min, between about 30 and 60 ft/min, between about 40 and 60 ft/min, between about 2 and 50 ft/min, between about 3 and 50 ft/min, between about 5 and 50 ft/min, between about 6 and 50 ft/min, between about 7 and 50 ft/min, between about 8 and 50 ft/min, between about 9 and 50 ft/min, between about 10 and 50 ft/min, between about 15 and 50 ft/min, between about 20 and 50 ft/min, between about 30 and 50 ft/min, between about 40 and 50 ft/min). It is preferable that the material be conveyed at a constant rate, for example, to help maintain a constant irradiation of the material as it passes under the electron beam (e.g., shower, field).

The vibratory conveyors described can include screens used for sieving and sorting materials. Port openings on the side or bottom of the troughs can be used for sorting, selecting or removing specific materials, for example, by size or shape. Some conveyors have counterbalances to reduce the dynamic forces on the support structure. Some vibratory conveyors are configured as spiral elevators, are designed to curve around surfaces and/or are designed to drop material from one conveyor to another (e.g., in a step, cascade or as a series of steps or a stair). Along with conveying materials conveyors can be used, by themselves or coupled with other equipment or systems, for screening, separating, sorting, classifying, distributing, sizing, inspection, picking, metal removing, freezing, blending, mixing, orienting, heating, cooking, drying, dewatering, cleaning, washing, leaching, quenching, coating, de-dusting and/or feeding. The conveyors can also include covers (e.g., dust-tight covers), side discharge gates, bottom discharge gates, special liners (e.g., anti-stick, stainless steel, rubber, custom steal, and or grooved), divided troughs, quench pools, screens, perforated plates, detectors (e.g., metal detectors), high temperature designs, food grade designs, heaters, dryers and or coolers. In addition, the trough can be of various shapes, for example, flat bottomed, vee shaped bottom, flanged at the top, curved bottom, flat with ridges in any direction, tubular, half pipe, covered or any combinations of these. In particular, the conveyors can be coupled with an irradiation systems and/or equipment.

The conveyors (e.g., vibratory conveyor) can be made of corrosion resistant materials. The conveyors can utilize structural materials that include stainless steel (e.g., 304, 316 stainless steel, HASTELLOY® ALLOYS and INCONEL® Alloys). For example, HASTELLOY® Corrosion-Resistant alloys from Hynes (Kokomo, Ind., USA) such as HASTELLOY® B-3® ALLOY, HASTELLOY® HYBRID-BC1® ALLOY, HASTELLOY® C-4 ALLOY, HASTELLOY® C-22® ALLOY, HASTELLOY® C-22HS® ALLOY, HASTELLOY® C-276 ALLOY, HASTELLOY® C-2000® ALLOY, HASTELLOY® G-30® ALLOY, HASTELLOY® G-35® ALLOY, HASTELLOY® N ALLOY and HASTELLOY® ULTIMET® alloy.

The vibratory conveyors can include non-stick release coatings, for example, TUFFLON™ (Dupont, Del., USA). The vibratory conveyors can also include corrosion resistant coatings. For example, coatings that can be supplied from Metal Coatings Corp (Houston, Tex., USA) and others such as Fluoropolymer, XYLAN®, Molybdenum Disulfide, Epoxy Phenolic, Phosphate-ferrous metal coating, Polyurethane-high gloss topcoat for epoxy, inorganic zinc, Poly Tetrafluoro ethylene, PPS/RYTON®, fluorinated ethylene propylene, PVDF/DYKOR®, ECTFE/HALAR® and Ceramic Epoxy Coating. The coatings can improve resistance to process gases (e.g., ozone), chemical corrosion, pitting corrosion, galling corrosion and oxidation.

Optionally, in addition to the conveying systems described herein, one or more other conveying systems can be enclosed. When using an enclosure, the enclosed conveyor can also be purged with an inert gas so as to maintain an atmosphere at a reduced oxygen level. Keeping oxygen levels low avoids the formation of ozone which in some instances is undesirable due to its reactive and toxic nature. For example, the oxygen can be less than about 20% (e.g., less than about 10%, less than about 1%, less than about 0.1%, less than about 0.01%, or even less than about 0.001% oxygen). Purging can be done with an inert gas including, but not limited to, nitrogen, argon, helium or carbon dioxide. This can be supplied, for example, from a boil off of a liquid source (e.g., liquid nitrogen or helium), generated or separated from air in situ, or supplied from tanks. The inert gas can be recirculated and any residual oxygen can be removed using a catalyst, such as a copper catalyst bed. Alternatively, combinations of purging, recirculating and oxygen removal can be done to keep the oxygen levels low.

The enclosed conveyor can also be purged with a reactive gas that can react with the biomass. This can be done before, during or after the irradiation process. The reactive gas can be, but is not limited to, nitrous oxide, ammonia, oxygen, ozone, hydrocarbons, aromatic compounds, amides, peroxides, azides, halides, oxyhalides, phosphides, phosphines, arsines, sulfides, thiols, boranes and/or hydrides. The reactive gas can be activated in the enclosure, e.g., by irradiation (e.g., electron beam, UV irradiation, microwave irradiation, heating, IR radiation), so that it reacts with the biomass. The biomass itself can be activated, for example by irradiation. Preferably the biomass is activated by the electron beam, to produce radicals which then react with the activated or unactivated reactive gas, e.g., by radical coupling or quenching.

Purging gases supplied to an enclosed conveyor can also be cooled, for example below about 25° C., below about 0° C., below about −40° C., below about −80° C., below about −120° C. For example, the gas can be boiled off from a compressed gas such as liquid nitrogen or sublimed from solid carbon dioxide. As an alternative example, the gas can be cooled by a chiller or part of or the entire conveyor can be cooled.

Other Embodiments

Any material, processes or processed materials discussed herein can be used to make products and/or intermediates such as composites, fillers, binders, plastic additives, adsorbents and controlled release agents. The methods can include densification, for example, by applying pressure and heat to the materials. For example composites can be made by combining fibrous materials with a resin or polymer. For example radiation cross-linkable resin, e.g., a thermoplastic resin can be combined with a fibrous material to provide a fibrous material/cross-linkable resin combination. Such materials can be, for example, useful as building materials, protective sheets, containers and other structural materials (e.g., molded and/or extruded products). Absorbents can be, for example, in the form of pellets, chips, fibers and/or sheets. Absorbents can be used, for example, as pet bedding, packaging material or in pollution control systems. Controlled release matrices can also be the form of, for example, pellets, chips, fibers and or sheets. The controlled release matrices can, for example, be used to release drugs, biocides, fragrances. For example, composites, absorbents and control release agents and their uses are described in International Serial No. PCT/US2006/010648, filed Mar. 23, 2006, and U.S. Pat. No. 8,074,910 filed Nov. 22, 2011, the entire disclosures of which are herein incorporated by reference.

In some instances the biomass material is treated at a first level to reduce recalcitrance, e.g., utilizing accelerated electrons, to selectively release one or more sugars (e.g., xylose). The biomass can then be treated to a second level to release one or more other sugars (e.g., glucose). Optionally the biomass can be dried between treatments. The treatments can include applying chemical and biochemical treatments to release the sugars. For example, a biomass material can be treated to a level of less than about 20 Mrad (e.g., less than about 15 Mrad, less than about 10 Mrad, less than about 5 Mrad, less than about 2 Mrad) and then treated with a solution of sulfuric acid, containing less than 10% sulfuric acid (e.g., less than about 9%, less than about 8%, less than about 7%, less than about 6%, less than about 5%, less than about 4%, less than about 3%, less than about 2%, less than about 1%, less than about 0.75%, less than about 0.50%, less than about 0.25%) to release xylose. Xylose, for example that is released into solution, can be separated from solids and optionally the solids washed with a solvent/solution (e.g., with water and/or acidified water). Optionally, the Solids can be dried, for example in air and/or under vacuum optionally with heating (e.g., below about 150 deg C., below about 120 deg C.) to a water content below about 25 wt. % (below about 20 wt. %, below about 15 wt. %, below about 10 wt. %, below about 5 wt. %). The solids can then be treated with a level of less than about 30 Mrad (e.g., less than about 25 Mrad, less than about 20 Mrad, less than about 15 Mrad, less than about 10 Mrad, less than about 5 Mrad, less than about 1 Mrad or even not at all) and then treated with an enzyme (e.g., a cellulase) to release glucose. The glucose (e.g., glucose in solution) can be separated from the remaining solids. The solids can then be further processed, for example utilized to make energy or other products (e.g., lignin derived products).

Flavors, Fragrances and Colorants

Any of the products and/or intermediates described herein, for example, produced by the processes, systems and/or equipment described herein, can be combined with flavors, fragrances, colorants and/or mixtures of these. For example, any one or more of (optionally along with flavors, fragrances and/or colorants) sugars, organic acids, fuels, polyols, such as sugar alcohols, biomass, fibers and composites can be combined with (e.g., formulated, mixed or reacted) or used to make other products. For example, one or more such product can be used to make soaps, detergents, candies, drinks (e.g., cola, wine, beer, liquors such as gin or vodka, sports drinks, coffees, teas), syrups, pharmaceuticals, adhesives, sheets (e.g., woven, none woven, filters, tissues) and/or composites (e.g., boards). For example, one or more such product can be combined with herbs, flowers, petals, spices, vitamins, potpourri, or candles. For example, the formulated, mixed or reacted combinations can have flavors/fragrances of grapefruit, orange, apple, raspberry, banana, lettuce, celery, cinnamon, chocolate, vanilla, peppermint, mint, onion, garlic, pepper, saffron, ginger, milk, wine, beer, tea, lean beef, fish, clams, olive oil, coconut fat, pork fat, butter fat, beef bouillon, legume, potatoes, marmalade, ham, coffee and cheeses.

Flavors, fragrances and colorants can be added in any amount, such as between about 0.001 wt. % to about 30 wt. %, e.g., between about 0.01 to about 20, between about 0.05 to about 10, or between about 0.1 wt. % to about 5 wt. %. These can be formulated, mixed and or reacted (e.g., with any one of more product or intermediate described herein) by any means and in any order or sequence (e.g., agitated, mixed, emulsified, gelled, infused, heated, sonicated, and/or suspended). Fillers, binders, emulsifier, antioxidants can also be utilized, for example protein gels, starches and silica.

In one embodiment the flavors, fragrances and colorants can be added to the biomass immediately after the biomass is irradiated such that the reactive sites created by the irradiation may react with reactive compatible sites of the flavors, fragrances, and colorants.

The flavors, fragrances and colorants can be natural and/or synthetic materials. These materials can be one or more of a compound, a composition or mixtures of these (e.g., a formulated or natural composition of several compounds). Optionally the flavors, fragrances, antioxidants and colorants can be derived biologically, for example, from a fermentation process (e.g., fermentation of saccharified materials as described herein). Alternatively, or additionally these flavors, fragrances and colorants can be harvested from a whole organism (e.g., plant, fungus, animal, bacteria or yeast) or a part of an organism. The organism can be collected and or extracted to provide color, flavors, fragrances and/or antioxidant by any means including utilizing the methods, systems and equipment described herein, hot water extraction, supercritical fluid extraction, chemical extraction (e.g., solvent or reactive extraction including acids and bases), mechanical extraction (e.g., pressing, comminuting, filtering), utilizing an enzyme, utilizing a bacteria such as to break down a starting material, and combinations of these methods. The compounds can be derived by a chemical reaction, for example, the combination of a sugar (e.g., as produced as described herein) with an amino acid (Maillard reaction). The flavor, fragrance, antioxidant and/or colorant can be an intermediate and or product produced by the methods, equipment or systems described herein, for example and ester and a lignin derived product.

Some examples of flavor, fragrances or colorants are polyphenols. Polyphenols are pigments responsible for the red, purple and blue colorants of many fruits, vegetables, cereal grains, and flowers. Polyphenols also can have antioxidant properties and often have a bitter taste. The antioxidant properties make these important preservatives. On class of polyphenols are the flavonoids, such as Anthocyanidines, flavanonols, flavan-3-ols, s, flavanones and flavanonols. Other phenolic compounds that can be used include phenolic acids and their esters, such as chlorogenic acid and polymeric tannins.

Among the colorants inorganic compounds, minerals or organic compounds can be used, for example titanium dioxide, zinc oxide, aluminum oxide, cadmium yellow (E.g., CdS), cadmium orange (e.g., CdS with some Se), alizarin crimson (e.g., synthetic or non-synthetic rose madder), ultramarine (e.g., synthetic ultramarine, natural ultramarine, synthetic ultramarine violet), cobalt blue, cobalt yellow, cobalt green, viridian (e.g., hydrated chromium(III)oxide), chalcophylite, conichalcite, cornubite, cornwallite and liroconite. Black pigments such as carbon black and self-dispersed blacks may be used.

Some flavors and fragrances that can be utilized include ACALEA TBHQ, ACET C-6, ALLYL AMYL GLYCOLATE, ALPHA TERPINEOL, AMBRETTOLIDE, AMBRINOL 95, ANDRANE, APHERMATE, APPLELIDE, BACDANOL®, BERGAMAL, BETA IONONE EPDXIDE, BETA NAPHTHYL ISO-BUTYL ETHER, BICYCLONONALACTONE, BORNAFIX®, CANTHOXAL, CASHMERAN®, CASHMERAN® VELVET, CASSIFFIX®, CEDRAFIX, CEDRAMBER®, CEDRYL ACETATE, CELESTOLIDE, CINNAMALVA, CITRAL DIMETHYL ACETATE, CITROLATE™, CITRONELLOL 700, CITRONELLOL 950, CITRONELLOL COEUR, CITRONELLYL ACETATE, CITRONELLYL ACETATE PURE, CITRONELLYL FORMATE, CLARYCET, CLONAL, CONIFERAN, CONIFERAN PURE, CORTEX ALDEHYDE 50% PEOMOSA, CYCLABUTE, CYCLACET®, CYCLAPROP®, CYCLEMAX™, CYCLOHEXYL ETHYL ACETATE, DAMASCOL, DELTA DAMASCONE, DIHYDRO CYCLACET, DIHYDRO MYRCENOL, DIHYDRO TERPINEOL, DIHYDRO TERPINYL ACETATE, DIMETHYL CYCLORMOL, DIMETHYL OCTANOL PQ, DIMYRCETOL, DIOLA, DIPENTENE, DULCINYL® RECRYSTALLIZED, ETHYL-3-PHENYL GLYCIDATE, FLEURAMONE, FLEURANIL, FLORAL SUPER, FLORALOZONE, FLORIFFOL, FRAISTONE, FRUCTONE, GALAXOLIDE® 50, GALAXOLIDE® 50 BB, GALAXOLIDE® 50 IPM, GALAXOLIDE® UNDILUTED, GALBASCONE, GERALDEHYDE, GERANIOL 5020, GERANIOL 600 TYPE, GERANIOL 950, GERANIOL 980 (PURE), GERANIOL CFT COEUR, GERANIOL COEUR, GERANYL ACETATE COEUR, GERANYL ACETATE, PURE, GERANYL FORMATE, GRISALVA, GUAIYL ACETATE, HELIONAL™, HERBAC, HERBALIME™, HEXADECANOLIDE, HEXALON, HEXENYL SALICYLATE CIS 3-, HYACINTH BODY, HYACINTH BODY NO. 3, HYDRATROPIC ALDEHYDE.DMA, HYDROXYOL, INDOLAROME, INTRELEVEN ALDEHYDE, INTRELEVEN ALDEHYDE SPECIAL, IONONE ALPHA, IONONE BETA, ISO CYCLO CITRAL, ISO CYCLO GERANIOL, ISO E SUPER®, ISOBUTYL QUINOLINE, JASMAL, JESSEMAL®, KHARISMAL®, KHARISMAL® SUPER, KHUSINIL, KOAVONE®, KOHINOOL®, LIFFAROME™, LIMOXAL, LINDENOL™, LYRAL®, LYRAME SUPER, MANDARIN ALD 10% TRI ETH, CITR, MARITIMA, MCK CHINESE, MEIJIFF™, MELAFLEUR, MELOZONE, METHYL ANTHRANILATE, METHYL IONONE ALPHA EXTRA, METHYL IONONE GAMMA A, METHYL IONONE GAMMA COEUR, METHYL IONONE GAMMA PURE, METHYL LAVENDER KETONE, MONTAVERDI®, MUGUESIA, MUGUET ALDEHYDE 50, MUSK Z4, MYRAC ALDEHYDE, MYRCENYL ACETATE, NECTARATE™, NEROL 900, NERYL ACETATE, OCIMENE, OCTACETAL, ORANGE FLOWER ETHER, ORIVONE, ORRINIFF 25%, OXASPIRANE, OZOFLEUR, PAMPLEFLEUR®, PEOMOSA, PHENOXANOL®, PICONIA, PRECYCLEMONE B, PRENYL ACETATE, PRISMANTOL, RESEDA BODY, ROSALVA, ROSAMUSK, SANJINOL, SANTALIFF™, SYVERTAL, TERPINEOL, TERPINOLENE 20, TERPINOLENE 90 PQ, TERPINOLENE RECT., TERPINYL ACETATE, TERPINYL ACETATE JAX, TETRAHYDRO, MUGUOL®, TETRAHYDRO MYRCENOL, TETRAMERAN, TIMBERSILK™, TOBACAROL, TRIMOFIX® 0 TT, TRIPLAL®, TRIS AMBER®, VANORIS, VERDOX™, VERDOX™ HC, VERTENEX®, VERTENEX® HC, VERTOFIX® COEUR, VERTOLIFF, VERTOLIFF ISO, VIOLIFF, VIVALDIE, ZENOLIDE, ABS INDIA 75 PCT MIGLYOL, ABS MOROCCO 50 PCT DPG, ABS MOROCCO 50 PCT TEC, ABSOLUTE FRENCH, ABSOLUTE INDIA, ABSOLUTE MD 50 PCT BB, ABSOLUTE MOROCCO, CONCENTRATE PG, TINCTURE 20 PCT, AMBERGRIS, AMBRETTE ABSOLUTE, AMBRETTE SEED OIL, ARMOISE OIL 70 PCT THUYONE, BASIL ABSOLUTE GRAND VERT, BASIL GRAND VERT ABS MD, BASIL OIL GRAND VERT, BASIL OIL VERVEINA, BASIL OIL VIETNAM, BAY OIL TERPENELESS, BEESWAX ABS N G, BEESWAX ABSOLUTE, BENZOIN RESINOID SIAM, BENZOIN RESINOID SIAM 50 PCT DPG, BENZOIN RESINOID SIAM 50 PCT PG, BENZOIN RESINOID SIAM 70.5 PCT TEC, BLACKCURRANT BUD ABS 65 PCT PG, BLACKCURRANT BUD ABS MD 37 PCT TEC, BLACKCURRANT BUD ABS MIGLYOL, BLACKCURRANT BUD ABSOLUTE BURGUNDY, BOIS DE ROSE OIL, BRAN ABSOLUTE, BRAN RESINOID, BROOM ABSOLUTE ITALY, CARDAMOM GUATEMALA CO2 EXTRACT, CARDAMOM OIL GUATEMALA, CARDAMOM OIL INDIA, CARROT HEART, CASSIE ABSOLUTE EGYPT, CASSIE ABSOLUTE MD 50 PCT IPM, CASTOREUM ABS 90 PCT TEC, CASTOREUM ABS C 50 PCT MIGLYOL, CASTOREUM ABSOLUTE, CASTOREUM RESINOID, CASTOREUM RESINOID 50 PCT DPG, CEDROL CEDRENE, CEDRUS ATLANTICA OIL REDIST, CHAMOMILE OIL ROMAN, CHAMOMILE OIL WILD, CHAMOMILE OIL WILD LOW LIMONENE, CINNAMON BARK OIL CEYLAN, CISTE ABSOLUTE, CISTE ABSOLUTE COLORLESS, CITRONELLA OIL ASIA IRON FREE, CIVET ABS 75 PCT PG, CIVET ABSOLUTE, CIVET TINCTURE 10 PCT, CLARY SAGE ABS FRENCH DECOL, CLARY SAGE ABSOLUTE FRENCH, CLARY SAGE C'LESS 50 PCT PG, CLARY SAGE OIL FRENCH, COPAIBA BALSAM, COPAIBA BALSAM OIL, CORIANDER SEED OIL, CYPRESS OIL, CYPRESS OIL ORGANIC, DAVANA OIL, GALBANOL, GALBANUM ABSOLUTE COLORLESS, GALBANUM OIL, GALBANUM RESINOID, GALBANUM RESINOID 50 PCT DPG, GALBANUM RESINOID HERCOLYN BHT, GALBANUM RESINOID TEC BHT, GENTIANE ABSOLUTE MD 20 PCT BB, GENTIANE CONCRETE, GERANIUM ABS EGYPT MD, GERANIUM ABSOLUTE EGYPT, GERANIUM OIL CHINA, GERANIUM OIL EGYPT, GINGER OIL 624, GINGER OIL RECTIFIED SOLUBLE, GUAIACWOOD HEART, HAY ABS MD 50 PCT BB, HAY ABSOLUTE, HAY ABSOLUTE MD 50 PCT TEC, HEALINGWOOD, HYSSOP OIL ORGANIC, IMMORTELLE ABS YUGO MD 50 PCT TEC, IMMORTELLE ABSOLUTE SPAIN, IMMORTELLE ABSOLUTE YUGO, JASMIN ABS INDIA MD, JASMIN ABSOLUTE EGYPT, JASMIN ABSOLUTE INDIA, ASMIN ABSOLUTE MOROCCO, JASMIN ABSOLUTE SAMBAC, JONQUILLE ABS MD 20 PCT BB, JONQUILLE ABSOLUTE France, JUNIPER BERRY OIL FLG, JUNIPER BERRY OIL RECTIFIED SOLUBLE, LABDANUM RESINOID 50 PCT TEC, LABDANUM RESINOID BB, LABDANUM RESINOID MD, LABDANUM RESINOID MD 50 PCT BB, LAVANDIN ABSOLUTE H, LAVANDIN ABSOLUTE MD, LAVANDIN OIL ABRIAL ORGANIC, LAVANDIN OIL GROSSO ORGANIC, LAVANDIN OIL SUPER, LAVENDER ABSOLUTE H, LAVENDER ABSOLUTE MD, LAVENDER OIL COUMARIN FREE, LAVENDER OIL COUMARIN FREE ORGANIC, LAVENDER OIL MAILLETTE ORGANIC, LAVENDER OIL MT, MACE ABSOLUTE BB, MAGNOLIA FLOWER OIL LOW METHYL EUGENOL, MAGNOLIA FLOWER OIL, MAGNOLIA FLOWER OIL MD, MAGNOLIA LEAF OIL, MANDARIN OIL MD, MANDARIN OIL MD BHT, MATE ABSOLUTE BB, MOSS TREE ABSOLUTE MD TEX IFRA 43, MOSS-OAK ABS MD TEC IFRA 43, MOSS-OAK ABSOLUTE IFRA 43, MOSS-TREE ABSOLUTE MD IPM IFRA 43, MYRRH RESINOID BB, MYRRH RESINOID MD, MYRRH RESINOID TEC, MYRTLE OIL IRON FREE, MYRTLE OIL TUNISIA RECTIFIED, NARCISSE ABS MD 20 PCT BB, NARCISSE ABSOLUTE FRENCH, NEROLI OIL TUNISIA, NUTMEG OIL TERPENELESS, OEILLET ABSOLUTE, OLIBANUM RESINOID, OLIBANUM RESINOID BB, OLIBANUM RESINOID DPG, OLIBANUM RESINOID EXTRA 50 PCT DPG, OLIBANUM RESINOID MD, OLIBANUM RESINOID MD 50 PCT DPG, OLIBANUM RESINOID TEC, OPOPONAX RESINOID TEC, ORANGE BIGARADE OIL MD BHT, ORANGE BIGARADE OIL MD SCFC, ORANGE FLOWER ABSOLUTE TUNISIA, ORANGE FLOWER WATER ABSOLUTE TUNISIA, ORANGE LEAF ABSOLUTE, ORANGE LEAF WATER ABSOLUTE TUNISIA, ORRIS ABSOLUTE ITALY, ORRIS CONCRETE 15 PCT IRONE, ORRIS CONCRETE 8 PCT IRONE, ORRIS NATURAL 15 PCT IRONE 4095C, ORRIS NATURAL 8 PCT IRONE 2942C, ORRIS RESINOID, OSMANTHUS ABSOLUTE, OSMANTHUS ABSOLUTE MD 50 PCT BB, PATCHOULI HEART N° 3, PATCHOULI OIL INDONESIA, PATCHOULI OIL INDONESIA IRON FREE, PATCHOULI OIL INDONESIA MD, PATCHOULI OIL REDIST, PENNYROYAL HEART, PEPPERMINT ABSOLUTE MD, PETITGRAIN BIGARADE OIL TUNISIA, PETITGRAIN CITRONNIER OIL, PETITGRAIN OIL PARAGUAY TERPENELESS, PETITGRAIN OIL TERPENELESS STAB, PIMENTO BERRY OIL, PIMENTO LEAF OIL, RHODINOL EX GERANIUM CHINA, ROSE ABS BULGARIAN LOW METHYL EUGENOL, ROSE ABS MOROCCO LOW METHYL EUGENOL, ROSE ABS TURKISH LOW METHYL EUGENOL, ROSE ABSOLUTE, ROSE ABSOLUTE BULGARIAN, ROSE ABSOLUTE DAMASCENA, ROSE ABSOLUTE MD, ROSE ABSOLUTE MOROCCO, ROSE ABSOLUTE TURKISH, ROSE OIL BULGARIAN, ROSE OIL DAMASCENA LOW METHYL EUGENOL, ROSE OIL TURKISH, ROSEMARY OIL CAMPHOR ORGANIC, ROSEMARY OIL TUNISIA, SANDALWOOD OIL INDIA, SANDALWOOD OIL INDIA RECTIFIED, SANTALOL, SCHINUS MOLLE OIL, ST JOHN BREAD TINCTURE 10 PCT, STYRAX RESINOID, STYRAX RESINOID, TAGETE OIL, TEA TREE HEART, TONKA BEAN ABS 50 PCT SOLVENTS, TONKA BEAN ABSOLUTE, TUBEROSE ABSOLUTE INDIA, VETIVER HEART EXTRA, VETIVER OIL HAITI, VETIVER OIL HAITI MD, VETIVER OIL JAVA, VETIVER OIL JAVA MD, VIOLET LEAF ABSOLUTE EGYPT, VIOLET LEAF ABSOLUTE EGYPT DECOL, VIOLET LEAF ABSOLUTE FRENCH, VIOLET LEAF ABSOLUTE MD 50 PCT BB, WORMWOOD OIL TERPENELESS, YLANG EXTRA OIL, YLANG III OIL and combinations of these.

The colorants can be among those listed in the Color Index International by the Society of Dyers and Colourists. Colorants include dyes and pigments and include those commonly used for coloring textiles, paints, inks and inkjet inks. Some colorants that can be utilized include carotenoids, arylide yellows, diarylide yellows, β-naphthols, naphthols, benzimidazolones, disazo condensation pigments, pyrazolones, nickel azo yellow, phthalocyanines, quinacridones, perylenes and perinones, isoindolinone and isoindoline pigments, triarylcarbonium pigments, diketopyrrolopyrrole pigments, thioindigoids. Cartenoids include, for example, alpha-carotene, beta-carotene, gamma-carotene, lycopene, lutein and astaxanthin, Annatto extract, Dehydrated beets (beet powder), Canthaxanthin, Caramel, β-Apo-8'-carotenal, Cochineal extract, Carmine, Sodium copper chlorophyllin, Toasted partially defatted cooked cottonseed flour, Ferrous gluconate, Ferrous lactate, Grape color extract, Grape skin extract (enocianina), Carrot oil, Paprika, Paprika oleoresin, Mica-based pearlescent pigments, Riboflavin, Saffron, Titanium dioxide, Tomato lycopene extract; tomato lycopene concentrate, Turmeric, Turmeric oleoresin, FD&C Blue No. 1, FD&C Blue No. 2, FD&C Green No. 3, Orange B, Citrus Red No. 2, FD&C Red No. 3, FD&C Red No. 40, FD&C Yellow No. 5, FD&C Yellow No. 6, Alumina (dried aluminum hydroxide), Calcium carbonate, Potassium sodium copper chlorophyllin (chlorophyllin-copper complex), Dihydroxyacetone, Bismuth oxychloride, Ferric ammonium ferrocyanide, Ferric ferrocyanide, Chromium hydroxide green, Chromium oxide greens, Guanine, Pyrophyllite, Talc, Aluminum powder, Bronze powder, Copper powder, Zinc oxide, D&C Blue No. 4, D&C Green No. 5, D&C Green No. 6, D&C Green No. 8, D&C Orange No. 4, D&C Orange No. 5, D&C Orange No. 10, D&C Orange No. 11, FD&C Red No. 4, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, D&C Red No. 39, D&C Violet No. 2, D&C Yellow No. 7, Ext. D&C Yellow No. 7, D&C Yellow No. 8, D&C Yellow No. 10, D&C Yellow No. 11, D&C Black No. 2, D&C Black No. 3 (3), D&C Brown No. 1, Ext. D&C, Chromium-cobalt-aluminum oxide, Ferric ammonium citrate, Pyrogallol, Logwood extract, 1,4-Bis[(2-hydroxy-ethyl)amino]-9,10-anthracenedione bis(2-propenoic) ester copolymers, 1,4-Bis [(2-methylphenyl)amino]-9,10-anthracenedione, 1,4-Bis[4-(2-methacryloxyethyl) phenylamino] anthraquinone copolymers, Carbazole violet, Chlorophyllin-copper complex, Chromium-cobalt-aluminum oxide, C.I. Vat Orange 1, 2-[[2,5-Diethoxy-4-[(4-methylphenyl)thiol] phenyl]azo]-1,3,5-benzenetriol, 16,23-Dihydrodinaphtho [2,3-a:2',3'-i] naphth [2',3': 6,7] indolo [2,3-c] carbazole-5,10,15,17,22,24-hexone, N,N'-(9,10-Dihydro-9,10-dioxo-1,5-anthracenediyl) bisbenzamide, 7,16-Dichloro- 6,15-dihydro-5,9,14,18-anthrazinetetrone, 16,17-Dimethoxydinaphtho (1,2,3-cd:3',2',1'-lm) perylene-5,10-dione, Poly(hydroxyethyl methacrylate)-dye copolymers(3), Reactive Black 5, Reactive Blue 21, Reactive Orange 78, Reactive Yellow 15, Reactive Blue No. 19, Reactive Blue No. 4, C.I. Reactive Red 11, C.I. Reactive Yellow 86, C.I. Reactive Blue 163, C.I. Reactive Red 180, 4-[(2,4-dimethylphenyl)azo]-2,4-dihydro-5-methyl-2-phenyl-3H-pyrazol-3-one (solvent Yellow 18), 6-Ethoxy-2-(6-ethoxy-3-oxobenzo[b]thien-2(3H)-ylidene) benzo[b]thiophen-3(2H)-one, Phthalocyanine green, Vinyl alcohol/methyl methacrylate-dye reaction products, C.I. Reactive Red 180, C.I. Reactive Black 5, C.I. Reactive Orange 78, C.I. Reactive Yellow 15, C.I. Reactive Blue 21, Disodium 1-amino-4-[[4-[(2-bromo-1-oxoallyl)amino]-2-sulphonatophenyl]amino]-9,10-dihydro-9,10-dioxoanthracene-2-sulphonate (Reactive Blue 69), D&C Blue No. 9, [Phthalocyaninato(2-)] copper and mixtures of these.

Other than in the examples herein, or unless otherwise expressly specified, all of the numerical ranges, amounts, values and percentages, such as those for amounts of materials, elemental contents, times and temperatures of reaction, ratios of amounts, and others, in the following portion of the specification and attached claims may be read as if prefaced by the word "about" even though the term "about" may not expressly appear with the value, amount, or range. Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains error necessarily resulting from the standard deviation found in its underlying respective testing measurements. Furthermore, when numerical ranges are set forth herein, these ranges are inclusive of the recited range end points (e.g., end points may be used). When percentages by weight are used herein, the numerical values reported are relative to the total weight.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10. The terms "one," "a," or "an" as used herein are intended to include "at least one" or "one or more," unless otherwise indicated.

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While this invention has been particularly shown and described with references to preferred embodiments thereof, it will be understood by those skilled in the art that various changes in form and details may be made therein without departing from the scope of the invention encompassed by the appended claims.

What is claimed is:

1. A system for processing a cellulosic or lignocellulosic material, the system comprising:
    a source of inert gas;
    a flow path for the inert gas, the flow path passing through an enclosed space, wherein the enclosed space is defined by a first foil in communication with the vacuum side of a scanning horn of an electron beam accelerator, and a secondary foil disposed facing the first foil window;
    a vault for irradiating the cellulosic or lignocellulosic material with an electron beam from the electron beam accelerator;
    and
    a treatment module for treating the inert gas;
    wherein the flow path includes a first conduit and an inlet for flowing the inert gas into the enclosed space, a second conduit in fluid communication with the first conduit, and an outlet for flowing the inert gas out of the space, and wherein the first conduit and/or inlet and second conduit and/or outlet are sized so that the pressure inside the space is above atmospheric pressure and the outlet is in fluid communication with the vault.

2. The system of claim 1 wherein the secondary foil is mounted on an enclosure.

3. The system of claim 2 wherein the pressure inside the enclosed space is between about 50 and 200 psi.

4. The system of claim 1, wherein the inert gas comprises nitrogen.

5. The system of claim 1, further comprising a recycling module for recycling the inert gas.

6. The system of claim 5, wherein the vault is in fluid communication with the recycling module.

7. The system of claim 6, wherein the recycling module is in fluid communication with the first conduit.

8. The system of claim 1, wherein the treatment module comprises a filter.

* * * * *